(12) United States Patent
Sorrentino et al.

(10) Patent No.: US 6,500,421 B1
(45) Date of Patent: Dec. 31, 2002

(54) IN VIVO SELECTION OF PRIMITIVE HEMATOPOIETIC CELLS

(75) Inventors: Brian P. Sorrentino, Memphis; Raymond L. Blakely, Germantown; James Allay, Cordova, all of TN (US); H. Trent Spencer, Columbia, SC (US)

(73) Assignee: St. Jude Children's Research Hospital, Nashville, TN (US)

( * ) Notice: Subject to any disclaimer, the term of this patent is extended or adjusted under 35 U.S.C. 154(b) by 0 days.

(21) Appl. No.: 09/297,749

(22) PCT Filed: Nov. 4, 1996

(86) PCT No.: PCT/US96/17660
§ 371 (c)(1),
(2), (4) Date: May 4, 1999

(87) PCT Pub. No.: WO98/19540
PCT Pub. Date: May 14, 1998

(51) Int. Cl.[7] .......................... A01N 63/00; C12N 15/00; C12N 5/00; C12N 15/86; A61K 48/00
(52) U.S. Cl. ................. 424/93.21; 435/320.1; 435/325; 435/456; 514/44; 530/385
(58) Field of Search ................... 514/44, 2; 530/385; 435/456, 320.1, 325; 424/93.21

(56) References Cited

U.S. PATENT DOCUMENTS 6,074,836 A * 6/2000 Bordignon et al. ......... 435/7.24

OTHER PUBLICATIONS

Orkin, et al. :Report and Recommendations of the Panel to Assess the NIH Investment in Research on Gene Therapy, www.nih.gov Dec. 1995.*
Verma et al. :Gene Therapy—promise , problems and prospects, Nature vol. 389, Sep. 1997, pp. 239–242.*
Crystal, R. Transfer of Genes to Humans: Early lessons and Obstacles to success: Science vol. 270, Oct. 20, 1995.*
Dang et al.Gene Therapy and Translational Cancer Therapy, Clinical Cancer Research, vol. 5, 471–474, Feb. 1999.*
Lewis, et al., Methotrexate–resistant Variants of Human Dihydrofolate Reductase with substitutions of Leucine 22, Journal of Biol. Chem. Mar. 10, 1995, vol. 270, No. 10. pp. 5057–5064.*
Hughes, et al. Potentiation of methotrexate lymphocytoxicity in vitro by inhibitors of nucleoside transport, Brit. J. Cancer (1989), 59, 381–384.*
Corey etal. Serial Transplantation of Methotrexate–Resistant Bone Marrow: Protection of Murine Recipients from drug toxicity by progeny of transduced stem cells, Blood 15, Jan. 1990, vol. 75, No. 2, pp. 337–343.*
Spencer, et al. A Gene Transfer Strategy for making bone marrow cells resistant trimetrexate, Blood: Mar. 15, 1996, vol. 87, No. 6, pp. 2579–2587.*
Flasshove et al. Ex Vivo Expansion and selection of Human CD34+ peripheral blood progenitor cells after introduction of a mutated dihydrofolate reductase cDNA via retroviral gene transfer, Blood, 15, Jan. 1995, vol. 85. No. 2, pp. 566–574.*
Thillet et al. , "Site directed mutagenesis of mouse dihydrofolate reductase", The Journal of Biological Chemistry, Sep. 5, 1988, vol. 263, No. 25, pp. 12500–12508.*
Corey et al., Serial transplantation of methotrexate–resistant bone marrow: protection of murine recipients from drug toxicity by progeny of transduced stem cells, 1990, Blood, vol. 72, No. 2, pp. 337–343.*
Hughes et al., Potentiation of methotrexate lymphocytoxicity in vitro by inhibitors of nucleoside transport.*
Karlsson, S. "Treatment of Genetic Defects in Hematopoietic Cell Function by Gene Transfer", Blood, vol. 78, No. 10, Nov. 15, 1991, pp. 2481–2492.
Dunbar, et al. "Retrovirally Marked CD34–Enriched Peripheral Blood and Bone Marrow Cells Contribute to Long–Term Engraftment After Autologous Transplantation", Blood, vol. 85, No. 11, Jun. 1, 1995, pp. 3048–3057.
Brenner, et al. "Gene marking to determine whether autologous marrow infusion restores long–term haemopoiesis in cancer patients", The Lancet, Nov. 6, 1993, vol. 342, pp. 1134–1137.
Simonsen, et al. "Isolation and expression of an altered mouse dihydrofolate reductase cDNA", Proc. Natl Acad. Sci. USA, vol. 80, May 1983, pp. 3495–2499.
Zhao et al. "Long–term protection of recipient mice lethal doses of methotrexate by marrow infected with a double–copy vector retrovirus containing a mutant dihydrofolate reductase", Cancer Gene Therapy, vol. 1, No. 1, 1994, pp. 27–33.
Blau, et al. "Cytokine Prestimulation as a Strategy for in vivo Selection: Resistance of Hemopoietic Progenitors to Folate Analogues." Stem Cell Gene Therapy: Biology and Technology, Sep. 28–Oct. 1, 1995.
Marina et al. "Effect of Nucleoside Transport Inhibitors on Thymidine Salvage and the Toxicity of Nucleoside Analogs in Mouse Bone Marrow Granulocyt–Macrophage Progenitor Cells", Cancer Communications, vol. 3, No. 12, 1991, pp. 367–372.

* cited by examiner

Primary Examiner—Deborah J. Reynolds
Assistant Examiner—Eleanor Sorbello

(57) ABSTRACT

The invention is directed to a method of in vivo selection for genetically modified hematopoietic progenitor cells from nonmodified hematopoietic cells in a subject. Ibis goal is accomplished by introducing mutant dihydrofolate reductase genes into hematopoietic progenitor cells and then administering to a subject harboring the resultant transformed cells an antifolate and a nucleoside transport inhibitor. The invention is also directed to nucleic acids encoding mutant dihydrofolate reductase genes and to hematopoietic cells transformed with such mutant genes.

28 Claims, 8 Drawing Sheets

IN VIVO SELECTION OF PRIMITIVE HEMATOPOIETIC CELLS

This invention was made with government support under Program Project Grant No. PO1 HL 53749-01 awarded by The National Heart, Lung, and Blood Institute, by the National Research Service Award No. T32 CA 09346, and by U.S. Public Health Service Grant No. PO1 CA 31922. The government has certain rights in the invention.

BACKGROUND OF THE INVENTION

1. Field of the Invention

This invention relates generally to selection of hematopoietic cells. Specifically, this invention relates to selection of hematopoietic progenitor and hematopoietic stem cells using a mutant dihydrofolate reductase in combination with a nucleoside transport inhibitor and an antifolate.

2. Background Art

Retroviral-mediated gene transfer is a potential therapeutic strategy for a number of diseases that affect the hematopoietic system. (Karlsson S. "Treatment of genetic defects in hematopoietic cell function by gene transfer." Blood 78:2481 (1991)). The early hematopoietic cells including hematopoietic progenitor cells and hematopoietic stem cells (HSC) are desirable targets for gene therapy. The hematopoietic stem cell is especially desirable for gene therapy because it can contribute progeny to all hematopoietic lineages and can support hematopoiesis throughout the lifetime of an animal. Despite these attractive features, primate HSCs remain relatively refractory to genetic modification. Although retroviral vectors provide one of the best methods for HSC transduction, recent clinical trials have shown that current protocols result in very low levels of HSC gene transfer. (Dunbar et al. "Retrovirally marked CD34-enriched peripheral blood and bone marrow cells contribute to long-term engraft ment after autologous transplantation." Blood 85:3048 (1995) and Brenner et al. "Gene marking to determine whether autologous marrow infusion restores long-term haemopoiesis in cancer patients." Lancet 342:1134 (1993)) Because the overall proportion of modified cells ranges from 10 to 0.01% after hematopoietic reconstitution, there are insufficient numbers of modified cells to be therapeutically effective. Thus, gene transfer is currently not a feasible treatment option for many diseases such as hemoglobinopathies, AIDS, chronic granulomatous disease, and cancer.

Because of the problem of low numbers of modified cells after hematopoietic reconstitution, selection of primitive HSCs is required for significant enrichment of modified cells. Selection of more differentiated cells would allow only a transient enrichment of modified cells due to the limited self-renewal capacity of these more mature cells.

One means of selecting modified cells that has been the focus of intense investigation involves dihydrofolate reductase. Dihydrofolate reductase is a ubiquitous cellular enzyme that catalyzes the generation of tetrahydrofolate, a necessary cofactor for purine and pyrimidine biosynthesis. Antifolate drugs such as methotrexate (MTX) are powerful inhibitors of DNA synthesis by virtue of their strong binding to the active site of DHFR. The discovery that single amino acid substitutions in the active site of DHFR could disrupt drug binding and thereby confer antifolate resistance (Simonsen et al. "Isolation and expression of an altered mouse dihydrofolate reductase cDNA." Proc. Anti. Acad. Sci. U S A 80:2495 (1983)) raised the possibility that mutant DHFRs could potentially be used as drug resistance genes.

Mutant DHFR genes were the first drug resistance genes to be transferred to primary hematopoietic cells. Despite the theoretical advantages for using DHFR as an in vivo selectable marker, and the potential protection of hematopoiesis conferred by DHPR variants, evidence for in vivo selection has been equivocal using this experimental system. In MTX-treated mice containing the murine L22R (leucine to arginine substitution at codon 22) variant of DHFR, there appeared to be an enrichment of vector-transduced CFU-S cells following MTX treatment. (Corey et al. "Serial transplantation of methotrexate-resistant bone marrow: protection of murine recipients from drug toxicity by progeny of transduced stem cells." Blood 75:337 (1990)) However, when Southern blot analysis was done to confirm an enrichment of vector-modified cells in myeloid tissue, no such enrichment could be documented. The authors suggested that more prolonged MTX exposure may be required for in vivo selection of DHFR-modified immature hematopoietic cells, thus implying that cell cycle status may play a significant role in antifolate resistance. In analogous experiments done using a human DHFR variant, only a 2-fold increase in vector-expressing myeloid progenitor cells was seen following MTX treatment. (Zhao et al. "Long-term protection of recipient mice from lethal doses of methotrexate by marrow infected with a double-copy vector retrovirus containing a mutant dihydrofolate reductase." Cancer Gene Therapy 1:27 (1994)) Hence, the authors conclude from this study that a modest level of in vivo selection of DHFR-modified progenitors can be accomplished utilizing MTX alone. However, several important controls were omitted from these experiments, such as the percentage of MTX resistant progenitors from DHFR mice that were not treated with MTX, so that even this modest level of selection remains unconvincing.

Another study reports that human myeloid progenitor cells transduced with a vector expressing a human DHFR variant were selected and expanded in vitro in MTX-containing cultures. (Flasshove et al. "Ex vivo expansion and selection of human CD34+ peripheral blood progenitor cells after introduction of a mutated dihydrofolate reductase cDNA via retroviral gene transfer." Blood 85:566 (1995)) Vector-expressing progenitor cells were amplified two-fold using this approach. However, this approach was in vitro. Further, it is not clear if transduced hematopoietic stem cells could be amplified using this method.

Consistent with these disappointing results, recent findings demonstrate that hematopoietic stem cells and progenitors are highly resistant to antifolates. (Blau et al. "Cytokine prestimulation as a strategy for in vivo selection: resistance of hemopoietic progenitors to folate analogs." Stem Cell Gene Therapy: Biology and Techniques. Sep. 28–Oct. 1 (1995)) These findings lead the authors to conclude that antifolates are poorly suited for the in vivo selection of transduced hematopoietic progenitor and stem cells. (Blau et al.).

The present invention overcomes these problems by disclosing a method which allows for effective elimination of unmodified hematopoietic cells which do not contain a transferred DHFR. The method thereby allows the modified hematopoietic progenitor and stem cells containing a modified DHFR to form a large proportion of the hematopoietic cells after reconstitution. To accomplish this result, the present method utilizes a nucleoside transport inhibitor to sensitize the non-modified hematopoietic cells to the antifolate. This invention, therefore, solves the problems identified by Blau et al. using a completely different approach.

"The use of nucleoside transport inhibitors has previously been proposed to potentiate the sensitivity of tumors to a variety of antifolates, including PALA, methotrexate, 5-fluorouracil, and acivicin, and potentially make these more effective by blocking the salvage of exogenous nucleosides. However, this use has produced perplexing results. It has been well demonstrated in cultured cell lines that exogenously added nucleosides can reverse the toxicity of these drugs and that nucleoside transport inhibitors such as NBMPR and dipyridamole can restore toxicity. (Marina et al. "Effect of nucleoside transport inhibitors on thymidine salvage and the toxicity of nucleoside analogs in mouse bone marrow granulocyte-macrophage progenitor cells." Cancer Communications 3:367 (1991)) However, in vivo studies with mice have shown either no antitumor effect of the transport inhibitor, no potentiation of the antitumor effect, or an increased somatic toxicity with little change in the therapeutic index. In addition, clinical phase I and II studies combining dipyridamole with acivicin, methotrexate, 5-fluorouracil, or PALA have revealed only limited responses."

Thus, this invention utilizes for the first time nucleoside transport inhibitors to select against unmodified hematopoietic progenitor and stem cells to provide an effective means to utilize gene therapy to treat many diseases of hematopoietic cells.

SUMMARY OF THE INVENTION

In accordance with the purpose(s) of this invention, as embodied and broadly described herein, this invention, in one aspect, provides a method of in vivo selection for genetically modified hematopoietic progenitor cells from nonmodified hematopoietic cells in a subject comprising genetically modifying hematopoietic progenitor cells by introducing into the cells a nucleic acid comprising a sequence encoding a mutant dihydrofolate reductase which, when expressed, can confer antifolate resistance, administering to the subject the genetically modified hematopoietic progenitor cells, administering to the subject an antifolate in an amount which inhibits the growth of the nonmodified hematopoietic cells, wherein the inhibition of the nonmodified hematopoietic cells by the antifolate can be offset in vivo by nucleoside salvage, and administering to the subject a suitable nucleoside transport inhibitor in an amount effective to prevent the offset of the inhibitory effect of the antifolate in the nonmodified hematopoietic cells, whereby the combination of the antifolate and the nucleoside transport inhibitor selects in vivo for the genetically modified hematopoietic progenitor cells.

The invention further provides a method of in vivo selection for hematopoietic progenitor cells genetically modified to contain and express a nucleic acid comprising a sequence encoding an antifolate resistant dihydrofolate reductase from nonmodified hematopoietic cells in a subject comprising administering to the subject the genetically modified hematopoietic progenitor cells, administering to the subject an antifolate in an amount which inhibits the growth of the nonmodified hematopoietic cells, wherein the inhibition of the nonmodified hematopoietic cells by the antifolate can be offset in vivo by nucleoside salvage, and administering to the subject a suitable nucleoside transport inhibitor in an amount effective to prevent the offset of the inhibitory effect of the antifolate in the nonmodified hematopoietic cells, whereby the combination of the antifolate and the nucleoside transport inhibitor selects in vivo for the genetically modified hematopoietic progenitor cells.

In another aspect, the invention provides a method of in vitro selecting for genetically modified hematopoietic progenitor cells from nonmodified hematopoietic cells comprising genetically modifying hematopoietic progenitor cells by introducing into the cells a nucleic acid comprising a sequence encoding a mutant dihydrofolate reductase which when expressed can confer antifolate resistance, administering to hematopoietic cells comprising the genetically modified hematopoietic progenitor cells and nonmodified hematopoietic cells an antifolate in an amount which inhibits the growth of the nonmodified hematopoietic cells, wherein the inhibition of the nonmodified hematopoietic cells by the antifolate can be offset by nucleoside salvage, and administering to the hematopoietic cells a suitable nucleoside transport inhibitor in an amount effective to prevent the offset of the inhibitory effect of the antifolate in the nonmodified hematopoietic cells, whereby the combination of the antifolate and the nucleoside transport inhibitor selects in vitro for the genetically modified hematopoietic progenitor cells.

In another aspect, the invention provides a method of in vitro selecting for genetically modified hematopoietic progenitor cells containing and expressing a nucleic acid comprising a sequence encoding an antifolate resistant dihydrofolate reductase from nonmodified hematopoietic cells comprising administering to hematopoietic cells comprising genetically modified hematopoietic progenitor cells and nonmodified hematopoietic cells an antifolate in an amount which inhibits the growth of the nonmodified hematopoietic cells, wherein the inhibition of the nonmodified hematopoietic cells by the antifolate can be offset by nucleoside salvage, and administering to the hematopoietic cells a suitable nucleoside transport inhibitor in an amount effective to prevent the offset of the inhibitory effect of the antifolate in the nonmodified hematopoietic cells, whereby the combination of the antifolate and the nucleoside transport inhibitor selects in vitro for the genetically modified hematopoietic progenitor cells.

In yet another aspect, the invention provides a method of in vivo selection for genetically modified hematopoietic progenitor cells from nonmodified hematopoietic cells in a subject comprising, genetically modifying hematopoietic progenitor cells in the subject by introducing into the cells a nucleic acid comprising a sequence encoding a mutant dihydrofolate reductase which when expressed can confer antifolate resistance, administering to the subject an antifolate in an amount which inhibits the growth of the nonmodified hematopoietic cells, wherein the inhibition of the nonmodified hematopoietic cells by the antifolate can be offset in vivo by nucleoside salvage, and administering to the subject a suitable nucleoside transport inhibitor in an amount effective to prevent the offset of the inhibitory effect of the antifolate in the nonmodified hematopoietic cells, whereby the combination of the antifolate and the nucleoside transport inhibitor selects in vivo for the genetically modified hematopoietic progenitor cells.

These selection methods are applicable to not only hematopoietic progenitor cells, but to hematopoietic stem cells as well. Additionally, the nucleic acid comprising a sequence encoding a dihydrofolate reductase which is relatively resistant to an antifolate can further comprise a heterologous gene. Using a nucleic acid further comprising a heterologous gene, the methods of the present invention can be used in gene therapy procedures.

The present invention further provides nucleic acids encoding mutant dihydrofolate reductases and cells expressing those nucleic acids.

DETAILED DESCRIPTION OF THE INVENTION

Figure 1A:
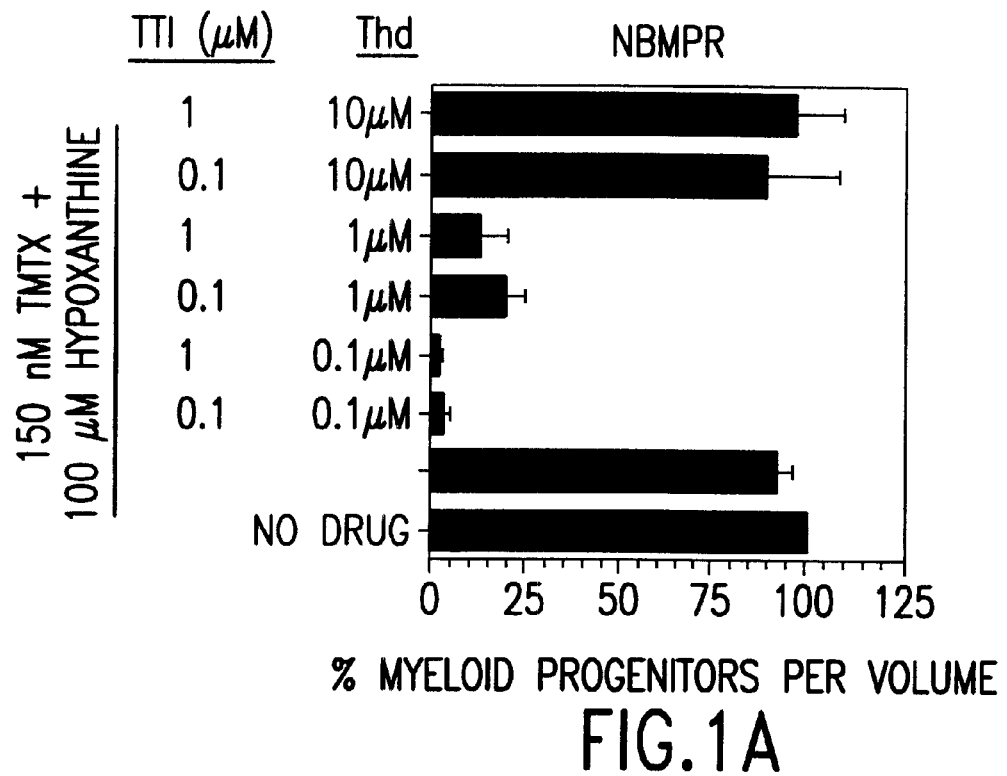
FIGS. 1a & 1b a show TTIs effectively block nucleoside salvage and potentiate TMTX toxicity at physiological concentrations of thymidine. Unseparated bone marrow from normal C57B1/6 or WBBF$_1$+/+ mice were cultured in DMEM plus dialyzed FBS with or without 150 nM TMTX, 100 mM hypoxanthine and 0.1, 1.0 or 10 $\mu$M thymidine. In addition, either A) NBMPR or B) draflazine at 0.1 or 1.0 $\mu$M were added to the indicated suspension cultures. Progenitors were assayed by a semisolid methylcellulose-based myeloid progenitor assay after four days of suspension culture.

The present invention may be understood more readily by reference to the following detailed description of the preferred embodiments of the invention and the Example included therein and to the Figures and their previous and following description.

Before the present compounds, compositions, and methods are disclosed and described, it is to be understood that this invention is not limited to specific nucleoside transport inhibitors, specific subjects, i.e. humans as well as non-humans, specific mutant dihydrofolate reductases, specific antifolates, specific nucleic acids, specific analogs, or specific methods, as such may, of course, vary, and the numerous modifications and variations therein will be apparent to those skilled in the art. It is also to be understood that the terminology used herein is for the purpose of describing particular embodiments only and is not intended to be limiting.

As used in the specification and in the claims, "a" can mean one or more, depending upon the context in which it is used. Thus, for example, reference to "a hematopoietic cell" means that at least one hematopoietic cell is utilized.

In one aspect, the invention provides a method of in vivo selection for genetically modified hematopoietic progenitor cells from nonmodified hematopoietic cells in a subject comprising genetically modifying hematopoietic progenitor cells by introducing into the cells a nucleic acid comprising a sequence encoding a mutant dihydrofolate reductase which when expressed can confer antifolate resistance, administering to the subject the genetically modified hematopoietic progenitor cells, administering to the subject an antifolate in an amount which inhibits the growth of the nonmodified hematopoietic cells, wherein the inhibition of the nonmodified hematopoietic cells by the antifolate can be offset in vivo by nucleoside salvage, and administering to the subject a suitable nucleoside transport inhibitor in an amount effective to prevent the offset of the inhibitory effect of the antifolate in the nonmodified hematopoietic cells, whereby the combination of the antifolate and the nucleoside transport inhibitor selects in vivo for the genetically modified hematopoietic progenitor cells.

In another aspect, the present invention provides a method of in vivo selection for genetically modified hematopoietic stem cells from nonmodified hematopoietic stem cells in a subject comprising genetically modifying hematopoietic stem cells by introducing into the cells a nucleic acid comprising a sequence encoding a mutant dihydrofolate reductase which when expressed can confer antifolate resistance, administering to the subject the genetically modified hematopoietic stem cells, administering to the subject an antifolate in an amount which inhibits the growth of the nonmodified hematopoietic stem cells, wherein the inhibition of the nonmodified hematopoietic stem cells by the antifolate can be offset in vivo by nucleoside salvage, and administering to the subject a suitable nucleoside transport inhibitor in an amount effective to prevent the offset of the inhibitory effect of the antifolate in the nonmodified hematopoietic stem cells, whereby the combination of the antifolate and the nucleoside transport inhibitor selects in vivo for the genetically modified hematopoietic stem cells.

Hematopoietic progenitor cells and hematopoietic stem cells are well known in the art. Hematopoietic progenitor cells represent those cells which are derived early in hematopoiesis from hematopoietic stem cells and are committed to a specific differentiation path for each type of mature blood cell. Techniques are widely known in the art which are used to identify hematopoietic progenitor cells, such as their ability to form myeloid colonies in semisolid media (Inscove et al. Proc. Soc. Exp. Biol. Med. 134:33 (1970)), the ability to form large IL-1 responsive colonies in culture (Bertoncello et al. Exp. Hematol. 19:174 (1991)), the ability to form cobblestone colonies in stromal cultures (Breems et al. Leukemia 8:1095 (1994)), or the ability to sustain long-term in vitro cultures (Eaves et al. Semin Hematol. 28:126 (1991)). Similarly, there are techniques which are widely used to identify hematopoietic stem cells, such as the ability to reconstitute the hematopoietic system in lethally irradiated animals, the ability to reconstitute serially transplanted animals, the ability to promote either allogeneic or autologous engraftment in human patients, the ability to form colonies in the spleen of irradiated animals (Till et al. Radiat. Res. 14:213 (1961)), the ability to reconstitute hematopoiesis in xenografted animals (Kamel-Reid et al. Science 242:1706 (1988) and Srour et al. Blood 82:3333 (1993)), the ability to sustain long-term in vitro cultures (Shah et al. Blood 87:3563 (1996), or the pattern of surface antigen expression on the cell surface (Uchida et al. J. Exp. Med. 175:(1992) and Terstappen et al. Blood 77:1218 (1991)).

The term "selection" is a term familiar to one of ordinary skill in the art and is used herein to describe supporting or sustaining the growth of a particular cell versus a different cell. For example, by genetically modifying hematopoietic progenitor cells and hematopoietic stem cells so that these cells are relatively resistant to the inhibitory effects of an antifolate drug, these modified cells can be "selected" for in a mixed population of cells comprising modified cells and nonmodified cells when the population is treated with an antifolate. Under this type of procedure, the growth of the nonmodified cells in the population can be inhibited by the antifolate whereas the growth of the modified cells is either not inhibited, or is inhibited to a lesser degree than the nonmodified cells. The inhibition of the nonmodified cells is not necessarily complete and the resistance of the modified cells to the inhibitory effects of the antifolate is not necessarily total, but when these two types of cells are treated with comparable amounts of an antifolate, the genetically modified cells are less affected by the drug than the nonmodified cells, i.e. they are "relatively resistant." Therefore the genetically modified cells are able to outcompete and/or outgrow the nonmodified cells, which can result in the predominance of the modified cells from a mixed population of cells comprising genetically modified cells and nonmodified cells.

The term "genetically modified" is another term familiar to one of ordinary skill in the art and is used herein to describe either introducing into cells a nucleic acid comprising a sequence encoding a mutant dihydrofolate reductase which has been mutated versus the wild-type dihydrofolate reductase such that the mutant dihydrofolate reductase is relatively resistant to the inhibitory effects of an antifolate versus the wild-type dihydrofolate reductase. It is well known in the art that antifolates, such as aminopterin, methotrexate (amethopterin), trimetrexate, edatrexate, pyritrexim, trimethoprim, pyrimethamine, 5,10 dideazatetrahydrofolate, 10-ethyl-10-deaza-aminopterin, 10-propargyl-5,8 dideazafolate, and 2,4-diamino 5(3',4' dichlorophenyl) 6 methylpyrimidine (DDMP) block the reduction of dihydrofolate to tetrahydrofolate and thereby inhibit de novo synthesis of-nucleotides which ultimately leads to an inhibition of cell growth in certain cells dependent upon de novo nucleotide synthesis by inhibiting dihydrofolate reductase. Certain mutants of dihydrofolate reductase, however, are relatively resistant to the inhibitory effects of antifolate drugs and the presence and expression of genes encoding these mutant dihydrofolate reductases in a certain cell can render these cells relatively resistant to the inhibitory effects of the antifolates. Other mutations to the nucleic acid encoding the dihydrofolate reductase are possible, but as used herein, the term "genetically modified" refers to the specific alterations to the nucleic acid, and therefore changes in the polypeptide, which render the dihydrofolate reductase relatively resistant to the inhibitory effects of an antifolate. Therefore the term "nonmodified" is not limited to a nucleic acid encoding a dihydrofolate reductase or the dihydrofolate reductase itself being totally homologous to the wild-type nucleic acid or polypeptide, but this specifically refers to the absence of modifications which can render the polypeptide relatively resistant to the inhibitory effects of an antifolate.

Another important aspect of this invention is the use of nucleoside transport inhibitors to effectively render nonmodified hematopoietic cells more susceptible to the inhibitory effects of an antifolate in combination with a mutant dihydrofolate reductase which is relatively resistant to the inhibitory effects of an antifolate. The nucleoside transport inhibitor blocks the salvage of nucleosides which, in primitive hematopoietic cells such as hematopoietic progenitor cells and hematopoietic stem cells, can bypass the de novo nucleotide synthesis block induced by the antifolate. For example, the de novo synthesis of inosine monophosphate and therefore the de novo synthesis of dATP and dGTP is blocked by the inhibition of DHFR. This blockage, however, can be bypassed by a salvage pathway utilizing hypoxanthine. Similarly, the de novo synthesis of dTMP from dUMP is blocked by the inhibition of DHFR, but this blockage can be bypassed by the salvage pathway utilizing thymidine. Therefore nonmodified hematopoietic progenitor cells and nonmodified hematopoietic stem cells, when treated with a suitable nucleoside transport inhibitor and an antifolate, are unable to grow and replicate since DNA synthesis is inhibited. Examples of these nucleoside transport inhibitors which specifically block the salvage of thymidine include, but are not limited to dilazep, drafiazine, a 5' monophosphate derivative of nitrobenzylmercaptopurine riboside (NBMPR or NBMPR-P), dipyridamole, mioflazine, soluflazine, and R57974. For a general review of transport inhibitors, see Paterson et al.: In: *Gerlach, E. and Becker, B. F.* (eds).

"Topics and perspectives in adenosine research" Springer, Berlin Heidelberg, New York, pp 89, 1987.

One of ordinary skill in the art will readily appreciate there are many alternatives available in which the hematopoietic progenitor cells or the hematopoietic stem cells can be genetically modified. One example of such a technique is the use of retroviral vector systems which can package a recombinant retroviral genome containing a nucleic acid encoding a modified dihydrofolate reductase. (See e.s., Pastan et al. "A retrovirus carrying an MDR1 cDNA confers multidrug resistance and polarized expression of P-glycoprotein in MDCK cells." Proc. Nat. Acad. Sci. 85:4486 (1988) and Miller et al. "Redesign of retrovirus packaging cell lines: to avoid recombination leading to helper virus production." Mol. Cell Biol. 6:2895 (1986)). The produced recombinant retrovirus can then be used to infect and thereby deliver to the infected cells a nucleic acid encoding the mutant dihydrofolate reductase. The exact method of introducing the mutant dihydrofolate reductase into the cells is, of course, not limited to the use of retroviral vectors. Other techniques are widely available for this procedure including the use of adenoviral vectors (Mitani et al. "Transduction of human bone marrow by adenoviral vector." Human Gene Therapy 5:941–948 (1994)), adenoassociated viral vectors (Goodman et al. "Recombinant adenoassociated virus-mediated gene transfer into hematopoietic progenitor cells." Blood 84:1492–1500 (1994)), lentiviral vectors (Naidini et al. "In vivo gene delivery and stable transduction of nondividing cells by a lentiviral vector." Science 272:263–267 (1996)), pseudotyped retroviral vectors (Agrawal et al. "Cell-cycle kinetics and VSV-G pseudotyped retrovirus mediated gene transfer in blood-derived CD34+cells." Exp.Hematol. 24:738–747 (1996)), and physical transfection techniques (Schwarzenberger et al. "Targeted gene transfer to human hematopoietic progenitor cell lines through the c-kit receptor." Blood 87:472–478 (1996)). This invention can be used in conjunction with any of these or other commonly used gene transfer methods.

An important aspect of the present invention is that the nucleic acid comprising a sequence encoding a mutant dihydrofolate reductase which, when expressed, can confer antifolate resistance to hematopoietic progenitor cells and/or hematopoietic stem cells, or the nucleic acid comprising a sequence encoding an antifolate resistant dihydrofolate reductase which, when expressed, can confer antifolate resistance to hematopoietic progenitor cells and/or hematopoietic stem cells, can further comprise a heterologous gene. This additional sequence is not limited to the entire sequence comprising a "gene" but can comprise the sequence encoding the gene product. One skilled in the art will appreciate that the coding region of the gene can be operatively linked to an additional sequence, such as a promoter in a vector, whereby the nucleic acid is expressed and the gene product is produced. The heterologous gene can be any gene encoding a gene product having clinical usefulness, for example, any gene or gene product that directly or indirectly enhances the therapeutic effects of the cells. Alternatively, the heterologous gene can be any gene or gene product that allows the cells to exert a therapeutic effect that the cells would not otherwise exert. Examples of suitable heterologous genes, which can be used for genetic therapy, are for example, those that encode cytokines such as tumor necrosis factor (TNF), interleukins (for example, interleukins 1–12), interferons (alpha, beta, and gamma-interferons), T-cell receptor proteins and the Fc receptors for antigen-binding domains of antibodies, such as immunoglobulins. Other examples of gene therapy are the supplementation of genes of the host, that for some reason do not produce a functional gene product or insufficient gene product, with a wild-type gene or a modified gene, which when expressed by the host, can produce a gene product which alleviates the condition of the host which is a result of the specific disorder. Other examples of specific disorders (and the genetic target of treatment) which are treatable by genetic therapy are well known in the art and include hemoglobinopathies (β-globin), HIV infection, Lesch-Nyhan syndrome (HPRT), severe combined immunodeficiency (ADA, PNP), and gaucher (GC).

The hematopoietic progenitor cells or hematopoietic stem cells can be removed from a subject, modified outside the subject, and administered to the same subject after modification (e.g. autologous cells). Alternatively, the hematopoietic progenitor cells or hematopoietic stem cells can be from a different subject than the subject to whom they are to be administered as long as they are compatable so that the modified cells are not rejected by the subjects immune system. The methods for facilitating engraftment are well established in the art. See, for example, Torok-Storb et al. "Role of marrow microenvironment in engraftment and maintenance of allogeneic hematopoietic stem cells." Bone Marrow Transplant. 14 Suppl 4:S71–S73 (1994).

The particular hematopoietic cells which are to be genetically modified or those that are already genetically modified can be allogeneic with respect to the subject that is to receive the genetically modified cells. Additionally, the particular hematopoietic cells which are to be genetically modified or those that are already genetically modified can be xenogeneic with respect to the subject that is to receive the genetically modified cells. In either situation, it is contemplated that the genetically modified cells are or will become compatable to the host, either genetically or through immune suppression, so that the modified cells are not rejected by the subject's immune system.

In addition to genetically modifying hematopoietic progenitor cells or hematopoietic stem cells by introducing into those cells a nucleic acid encoding a mutant dihydrofolate reductase, these cells can also be genetically modified by techniques such as site-specific recombination or mutagenesis whereby an altered nucleic acid is exchanged for the wild-type nucleic acid within the cell or the wild-type nucleic acid is altered within the cell. Therefore genetically modifying cells by introducing into cells a nucleic acid comprising a sequence encoding a mutant dihydrofolate reductase is not limited to simply adding a modified nucleic acid to the cells, but also includes any technique whereby a modified nucleic acid comprising a sequence encoding a mutant dihydrofolate reductase is expressed in a cell that previously expressed a nucleic acid encoding a nonmodified dihydrofolate reductase. Alternatively, where a cell may express both a nucleic acid comprising a sequence encoding a modified dihydrofolate reductase and a nucleic acid encoding a nonmodified dihydrofolate reductase, genetically modifying these cells includes altering the expression of the nucleic acids such that the nucleic acid encoding the modified dihydrofolate reductase is favored to the extent that the cell is relatively resistant to the inhibitory effects of an antifolate. The methods described herein are not limited to specific methods in which each manipulation can be performed. The present invention describes the discovery of and claims the manipulation of cells whereby specific cells in a population, such as hematopoietic progenitor cells or-hematopoietic stem cells, can be selected.

These hematopoietic progenitor cells or hematopoietic stem cells, after being genetically modified by introducing into these cells a nucleic acid comprising a sequence encoding a mutant dihydrofolate reductase which is relatively resistant to an antifolate, are administered to a subject. This subject can be a human or any other mammal, such as canine, equine, feline, porcine, bovine, or non-human primates. One skilled in the art will readily appreciate that selecting these modified cells in subjects other than humans can have profound economic potential, such as in selection of a porcine hematopoietic stem cell that has been also or additionally modified (e.g. glycosylation patterns) such that the human immune system does not recognize the porcine cells as non-self. Cells such as these can be important for potential transplantation procedures.

The techniques used for administering the genetically modified hematopoietic progenitor cells or the genetically modified hematopoietic stem cells will be apparent to one of ordinary skill in the art. For example, these modified cells can be administered by I.V. to a patient in an amount sufficient to repopulate the patient's hematopoietic and immune system. Alternatively, the genetically modified cells can be directly introduced into a subject as a bone marrow administration. Precise, effective quantities can be readily determined by those skilled in the art and will depend, of course, upon the exact condition being treated, the severity of the condition, the size of the subject, etc. For general references for blood marrow transplant, see Brenner et al. "Gene marking to determine whether autologous marrow infusion restores long-term haemopoiesis in cancer patients." Lancet 342:1134 (1993) and Dunbar et al. "Retrovirally marked CD34-enriched peripheral blood and bone marrow cells contribute to long-term engraftment after autologous transplantation." Blood 85:3048 (1995).

The subject that is being administered the genetically modified hematopoietic progenitor cells or hematopoietic stem cells is also administered an antifolate in an amount which inhibits the growth of the nonmodified hematopoietic cells in the presence of a suitable nucleoside transport inhibitor. The effective amount of the antifolate can readily be determined by one skilled in the art and can typically range from 5 to 500 nM if the cells are selected in culture with trimetrexate or from 5 to 11 mg/square meter of body surface area given daily for five consecutive days where the cells are selected in vivo with trimetrexate. These dosages are exemplary only and are not meant to be limiting. The specific-dosage will of course vary, and may depend upon such variables such as the nucleoside transport inhibitor, the mass of the subject, the condition of the subject, the type and severity of the condition the subject is experiencing which requires therapy, the expression levels of nucleic acid encoding the nonmodified dihydrofolate reductase, etc. The therapeutically effective amount can readily be determined by routine optimization procedures.

The administration of the antifolate can have the additional advantage in certain subjects of inhibiting the growth of not only the nonmodified hematopoietic cells, but of other rapidly growing cells as well, such as cancer cells and especially certain types of leukemias. This type of selection, therefore, has the particular-advantage of being able to select for modified hematopoietic cells that have resistance to an antifolate in a subject that is being administered an antifolate as an anticancer chemotherapeutic. The modified hematopoietic cells can therefore divide and differentiate within a chemotherapy-patient so that the patient's hematopoietic system can become reestablished with these genetically modified hematopoietic cells which will also be resistant to further chemotherapy treatments.

As discussed above, the nucleoside transport inhibitor blocks the salvage pathway of nucleotide synthesis, specifically thymidylic acid synthesis; therefore cells exposed to a nucleoside transport inhibitor are dependent upon de novo thymidylic acid synthesis. This de novo synthesis can be blocked in cells by an antifolate which inhibits dihydrofolate reductase. Where the nucleoside transport inhibitor is not pressent, the inhibitory effects of the antifolate can be offset or rescued in nonmodified cells by the nucleotide salvage pathway. This offset or rescue from inhibitory effects of the antifolate can be either a complete elimination of the inhibitory effects or less than a complete offset or rescue where the inhibitory effects are reduced to the extent that the nonmodified hematopoietic cells are able to survive and grow despite some dependence on the de novo synthesis of thymidylic acid, but these cells cannot be selected against versus genetically modified hematopoietic progenitor cells or the genetically modified hematopoietic stem cells in the presence of an antifolate without a nucleoside transport inhibitor. The nucleoside transport inhibitor prevents this offset or rescue from the inhibitory effects of the antifolate such that genetically modified hematopoietic progenitor cells or genetically modified hematopoietic stem cells expressing a mutant nucleic acid encoding a dihydrofolate reductase which is resistant to an antifolate are able to grow and replicate in the presence of the antifolate and the nucleoside transport inhibitor whereas nonmodified hematopoietic cells cannot grow or replicate, or can only grow or replicate to a lesser degree. The nucleoside transport inhibitor which is suitable for use in the methods described herein are those which can inhibit nucleoside transport in vivo and/or in vitro, depending upon which method is utilized. The combination of the nucleic acid encoding a mutant dihydrofolate reductase which is resistant to an antifolate with the antifolate and the suitable. nucleoside transport inhibitor, therefore, allows the efficient selection of the genetically modified cells from a mixed population of cells comprising genetically modified cells and nonmodified cells.

As with the antifolate, one of ordinary skill in the art can readily determine the optimum dosage of the nucleoside transport inhibitor for the desired effect. A typical dosage of NBMPR-P can range from 60 to 100 mg disodium NBMPR-P dissolved in 250 ml saline over 2 hours via an intravenous infusion where the cells are selected in vivo in human subjects. These dosages are also exemplary only and are not meant to be limiting. This amount will of course vary, and will depend among variables such as the dosage of the antifolate, the concentration of nucleosides in the subject or culture, the mass of the subject, the condition of the subject, the schedule of administration of the antifolate and/or the nucleoside transport inhibitor, etc. The therapeutically effective amount can readily be determined by routine optimization procedures.

The nucleic acid encoding dihydrofolate reductase is well known to one of ordinary skill in the art. This enzyme is well known to be essential for the reduction of 7,8-dihydrofolate to 5,6,7,8-tetrahydrofolate which is required for the biosynthesis of thymidylate and purine nucleotides. Various mutations in the dihydrofolate reductase gene yield mutants with varying degrees of resistance to antifolate drugs. These mutants include Gly (G) to Trp (W) at codon 15, Leu (L) to Arg (R) or Leu (L) to Phe (F) or Leu (L) to Tyr (Y) at codon 22, and Phe (F) to Ser (S) or Phe (F) to Trp (W) or Phe (F) to Gly (G) at codon 31.

In a presently preferred embodiment of the invention, the mutant dihydrofolate reductase used in any of the selection methods described herein can comprise the dihydrofolate reductase containing a tyrosine at codon 22. This mutant represents a mutant with approximately 100-fold higher resistance to an antifolate than the wild-type dihydrofolate reductase. The use of this mutant as part of the selection method, therefore, can better enable one to select genetically modified hematopoietic progenitor cells or genetically modified hematopoietic stem cells.

The present invention also provides that the amino acid substitution of Arginine for Phenylalanine at codon 31 of dihydrofolate reductase can result in a mutant which is especially resistant to antifolates. Therefore in another aspect of the present invention, the mutant dihydrofolate reductase used in any of the selection methods described herein can comprise the dihydrofolate reductase containing an arginine at codon 31.

In another aspect of the present invention, the mutant dihydrofolate reductase used in any of the selection methods described herein can comprise the dihydrofolate reductase containing a double mutation: A presently preferred double mutation includes a tyrosine at codon 22 and an arginine at codon 31. Various other combinations including multiple mutations or later discovered mutations can also be utilized.

The present invention also provides purified mutant dihydrofolate reductases that are relatively resistant to the inhibitory effects of an antifolate. In one embodiment, the mutant dihydrofolate reductase has an arginine at codon 31. In another embodiment, the mutant dihydrofolate reductase has a tyrosine at codon 22 and an arginine at codon 31.

The mutant dihydrofolate reductases provided for by the present invention may be obtained in any number of ways. For example, a DNA molecule encoding a dihydrofolate reductase can be isolated from the organism in which it is normally found. For example, a genomic DNA or cDNA library can be constructed and screened for the presence of the nucleic acid of interest. Methods of constructing and screening such libraries are well known in the art and kits for performing the construction and screening steps are commercially available (for example,: Stratagene Cloning Systems, La Jolla, Calif.). Once isolated, the nucleic acid can be directly cloned into an appropriate vector, or if necessary, be modified to facilitate the subsequent cloning steps. Such modification steps are routine, an example of which is the addition of oligonucleotide linkers which contain restriction sites to the termini of the nucleic acid. General methods are set forth in Sambrook et al, "Molecular Cloning, a Laboratory Manual," Cold Spring Harbor Laboratory Press (1989).

A dihydrofolate reductase from any organism is contemplated. The example contained herein discloses the use of a mutant dihydrofolate reductase from humans. The methods, compounds, and compositions of the present invention, however, are not limited to this particular isolate as it is disclosed only as an exemplary model and any dihydrofolate reductase that either is modified such that it is relatively resistant to the inhibitory effects of an antifolate, or one that can be modified to be relatively resistant to the inhibitory effects of an antifolate, or one that is naturally relatively resistant to the inhibitory effects of an antifolate is contemplated. Thus, other species mutant dihydrofolate reductases can be utilized.

Once the nucleic acid sequence encoding the desired dihydrofolate reductase is obtained, any specific amino acid can be altered, if desired, at any particular amino acid position by techniques well known in the art. For example, PCR primers can be designed which span the amino acid position or positions and which can substitute a basic amino acid for a non-basic amino acid. Then a nucleic acid can be amplified and inserted into the wild-type dihydrofolate reductase coding sequence in order to obtain any of a number of possible combinations of basic amino acids at any position of the dihydrofolate reductase. Alternatively, one skilled in the art can introduce specific mutations at any point in a particular nucleic acid sequence through techniques for point mutagenesis. General methods are set forth in Smith, M. "In vitro mutagenesis" Ann. Rev. Gen., 19:423–462 (1985) and Zoller, M. J. "New molecular biology methods for protein engineering" Curr. Opin. Struct. Biol., 1:605–610 (1991).

Another example of a method of obtaining a DNA molecule encoding a specific dihydrofolate reductase is to synthesize a recombinant DNA molecule which encodes the dihydrofolate reductase. For example, oligonucleotide synthesis procedures are routine in the art and oligonucleotides coding for a particular protein region are readily obtainable through automated DNA synthesis. A nucleic acid for one strand of a double-stranded molecule can be synthesized and hybridized to its complementary strand. One can design these oligonucleotides such that the resulting double-stranded molecule has either internal restriction sites or appropriate 5' or 3' overhangs at the termini for cloning into an appropriate vector. Double-stranded molecules coding for relatively large proteins can readily be synthesized by first constructing several different double-stranded molecules that code for particular regions of the protein, followed by ligating these DNA molecules together. For example, Cunningham, et al., "Receptor and Antibody Epitopes in Human Growth Hormone Identified by Homolog-Scanning Mutagenesis," Science, 243:1330–1336 (1989), have constructed a synthetic gene encoding the human growth hormone gene by first constructing overlapping and complementary synthetic oligonucleotides and ligating these fragments together. See also, Ferreiti, et al., Proc. Nat. Acad. Sci. 82:599–603 (1986), wherein synthesis of a 1057 base pair synthetic bovine rhodopsin gene from synthetic oligonucleotides is disclosed. By constructing a nucleic acid encoding a dihydrofolate reductase in this manner, one skilled in the art can readily obtain any particular mutant dihydrofolate reductase with desired amino acid at any particular position or positions of the polypeptide. See also, U.S. Pat. No. 5,503,995 which describes an enzyme template reaction method of making synthetic genes. Techniques such as this are routine in the art and are well documented. DNA fragments encoding a dihydrofolate reductase can then be expressed in vivo or in vitro.

Once a nucleic acid encoding a particular dihydrofolate reductase of interest, or a region of that nucleic acid, is constructed, modified, or isolated, that nucleic acid can then be cloned into an appropriate vector, which can direct the in vivo or in vitro synthesis of that wild-type and/or modified dihydrofolate reductase. The vector is contemplated to have the necessary functional elements that direct and regulate transcription of the inserted gene, or hybrid gene. These functional elements include, but are not limited to, a promoter, regions upstream or downstream of the promoter, such as enhancers that may regulate the transcriptional activity of the promoter, an origin of replication, appropriate restriction sites to facilitate cloning of inserts adjacent to the promoter, antibiotic resistance genes or other markers which can serve to select for cells containing the vector or the vector containing the insert, RNA splice junctions, a transcription termination region, or any other region which may serve to facilitate the expression of the inserted gene or hybrid gene. (See generally, Sambrook et al.).

This invention also provides a nucleic acid comprising a sequence encoding a mutant dihydrofolate reductase containing an arginine at codon 31. In another embodiment, the invention provides a hematopoietic progenitor cell or a hematopoietic stem cell expressing a nucleic acid comprising a sequence encoding a mutant dihydrofolate reductase containing an arginine at codon 31.

This invention further provides a nucleic acid comprising a sequence encoding a mutant dihydrofolate reductase containing a tyrosine at codon 22 and an arginine at codon 31. In another embodiment, the invention provides a hematopoietic progenitor cell or a hematopoietic stem cell expressing a nucleic acid comprising a sequence encoding a mutant dihydrofolate reductase containing a tyrosine at codon 22 and an arginine at codon 31.

In one specific embodiment of the present invention, in any of the selection methods described herein, the mutant dihydrofolate reductase contains a tyrosine at codon 22 and the antifolate is trimetrexate:

In another specific embodiment of any of the selection methods described herein, the mutant dihydrofolate reductase contains a tyrosine at codon 22 and an arginine at codon 31 and the antifolate is trimetrexate.

The present invention also provides a method of in vivo selection for hematopoietic progenitor cells genetically modified to contain and express a nucleic acid comprising a sequence encoding an antifolate resistant dihydrofolate reductase from nonmodified hematopoietic cells in a subject comprising administering to the subject the genetically modified hematopoietic progenitor cells, administering to the subject an antifolate in an amount which inhibits the growth of the nonmodified hematopoietic cells, wherein the inhibition of the nonmodified hematopoietic cells by the antifolate can be offset in vivo by nucleoside salvage, and administering to the subject a suitable nucleoside transport inhibitor in an amount effective to prevent the offset of the inhibitory effect of the antifolate in the nonmodified hematopoietic cells, whereby the combination of the antifolate and the nucleoside transport inhibitor selects in vivo for the genetically modified hematopoietic progenitor cells.

The present invention further provides a method of in vivo selection for hematopoietic stem cells genetically modified to contain and express a nucleic acid comprising a sequence encoding an antifolate resistant dihydrofolate reductase from nonmodified hematopoietic stem cells in a subject comprising administering to the subject the genetically modified hematopoietic stem cells, administering to the subject an antifolate in an amount which inhibits the growth of the nonmodified hematopoietic stem cells, wherein the inhibition of the nonmodified hematopoietic stem cells by the antifolate can be offset in vivo by nucleoside salvage, and administering to the subject a suitable nucleoside transport inhibitor in an amount effective to prevent the offset of the inhibitory effect of the antifolate in the nonmodified hematopoietic stem cells, whereby the combination of the antifolate and the nucleoside transport inhibitor selects in vivo for the genetically modified hematopoietic stem cells.

In these selection methods, the genetically modified hematopoietic progenitor cells or the genetically modified hematopoietic stem cells have previously been genetically modified such that they contain and are capable of or can express a mutant dihydrofolate reductase which is resistant to an antifolate. As noted above, various mutant dihydrofolate reductases are known in the art and one of ordinary skill in the art will readily appreciate there are numerous commercial entities which can genetically modify hematopoietic progenitor cells and/or hematopoietic stem cells such that these cells contain and express a mutant dihydrofolate reductase for any number of purposes. For example, dihydrofolate reductase is commonly used as a gene targeted for inhibition by antifolates in the study of gene amplification. These genetically modified hematopoietic progenitor cells and genetically modified hematopoietic stem cells can be the subject of this type of study as well. It is not necessary, therefore, that the genetically modified hematopoietic progenitor cells or genetically modified hematopoietic stem cells be genetically modified for use specifically as a component of one of any of the methods described herein, but their use in any of these methods is contemplated.

The present invention also provides a method of in vitro selection for genetically modified hematopoietic progenitor cells from nonmodified hematopoietic cells comprising genetically modifying hematopoietic progenitor cells by introducing into the cells a nucleic acid comprising a sequence encoding a mutant dihydrofolate reductase which when expressed can confer antifolate resistance, administering to hematopoietic cells comprising the genetically modified hematopoietic progenitor cells and nonmodified hematopoietic cells an antifolate in an amount which inhibits the growth of the nonmodified hematopoietic cells, wherein the inhibition of the nonmodified hematopoietic cells by the antifolate can be offset by nucleoside salvage, and administering to the hematopoietic cells a suitable nucleoside transport inhibitor in an amount effective to prevent the offset of the inhibitory effect of the antifolate in the nonmodified hematopoietic cells, whereby the combination of the antifolate and the nucleoside transport inhibitor selects in vitro for the genetically modified hematopoietic progenitor cells.

The term "in vitro" is a term familiar to one of ordinary skill in the art and is used herein to describe selecting genetically modified hematopoietic progenitor cells from nonmodified hematopoietic cells outside the subject; i.e. in culture. Therefore the genetically modified cells, whether modified as part of a selection method or previously modified and later used in a selection method, can be selected for from a mixed population of cells comprising genetically modified hematopoietic progenitor cells and nonmodified hematopoietic cells. This selection in vitro has the advantage of allowing one to selectively propagate the genetically modified hematopoietic progenitor cells in vitro so that where these genetically modified cells are subsequently administered to a subject, the subject receives a higher percent of genetically modified cells versus nonmodified hematopoietic cells which can allow the subject, for example, to recover from a myeloablative procedure more rapidly than where the selection for the genetically modified hematopoietic progenitor cells is performed in vivo. Another advantage is that the subject is spared the toxic effects of drug selection. Antifolates not only cause myeolsuppression, they can also cause mucositis, nausea, vomiting, chemical hepatitis, dermatitis, and other side-effects. Therefore, in vitro selection spares the subject both the hematologic and non-hematologic side effects associated with antifolates and nucleoside transport inhibitors (which additionally can cause headache, nausea, low blood pressure, and a rapid heart rate).

A similar in vitro selection procedure can be performed for hematopoietic stem cells. The invention, therefore, also provides a method of in vitro selection for genetically modified hematopoietic stem cells from nonmodified hematopoietic stem cells comprising genetically modifying hematopoietic stem cells by introducing into the cells a nucleic acid comprising a sequence encoding a mutant dihydrofolate reductase which when expressed can confer antifolate resistance, administering to hematopoietic stem cells comprising the genetically modified hematopoietic stem cells and nonmodified hematopoietic stem cells an antifolate in an amount which inhibits the growth of the nonmodified hematopoietic stem cells, wherein the inhibition of the nonmodified hematopoietic stem cells by the antifolate can be offset by nucleoside salvage, and administering to the hematopoietic stem cells a suitable nucleoside transport inhibitor in an amount effective to prevent the offset of the inhibitory effect of the antifolate in the nonmodified hematopoietic stem cells, whereby the combination of the antifolate and the nucleoside transport inhibitor selects in vitro for the genetically modified hematopoietic stem cells.

This method allows one to select for genetically modified hematopoietic stem cells in vitro such that nonmodified cells or cells not expressing the mutant dihydrofolate reductase can be eliminated prior to administering the cells to the subject. Having the mutant dihydrofolate reductase allows one to use the same selection technique both in vivo and in vitro such that the genetically modified hematopoietic stem cells can, but need not be expanded prior to in vivo selection.

The present invention also provides a method of in vitro selecting for genetically modified hematopoietic progenitor cells containing and expressing a nucleic acid comprising a sequence encoding an antifolate resistant dihydrofolate reductase from nonmodified hematopoietic cells comprising administering to hematopoietic cells comprising genetically modified hematopoietic progenitor cells and nonmodified hematopoietic cells an antifolate in an amount which inhibits the growth of the nonmodified hematopoietic cells, wherein the inhibition of the nonmodified hematopoietic cells by the antifolate can be offset by nucleoside salvage, and administering to the hematopoietic cells a suitable nucleoside transport inhibitor in an amount effective to prevent the offset of the inhibitory effect of the antifolate in the nonmodified hematopoietic cells, whereby the combination of the antifolate and the nucleoside transport inhibitor selects in vitro for the genetically modified hematopoietic progenitor cells.

A similar in vitro selection procedure can also be performed for hematopoietic stem cells where genetically modifying the hematopoietic stem cell is not a part of the selection but where these modified cells are obtained elsewhere. Therefore the present invention also provides a method of in vitro selecting for genetically modified hematopoietic stem cells containing and expressing a nucleic acid comprising a sequence encoding an antifolate resistant dihydrofolate reductase from nonmodified hematopoietic stem cells comprising administering to hematopoietic stem cells comprising genetically modified hematopoietic stem cells and nonmodified hematopoietic stem cells an antifolate in an amount which inhibits the growth of the nonmodified hematopoietic stem cells, wherein the inhibition of the nonmodified hematopoietic stem cells by the antifolate can be offset by nucleoside salvage, and administering to the hematopoietic stem cells a suitable nucleoside transport inhibitor in an amount effective to prevent the offset of the inhibitory effect of the antifolate in the nonmodified hematopoietic stem cells, whereby the combination of the antifolate and the nucleoside transport inhibitor selects in vitro for the genetically modified hematopoietic stem cells.

In another aspect of the present invention, the genetic modification of the hematopoietic progenitor cells as well as the selection of the genetically modified hematopoietic progenitor cells can occur in the subject itself One of ordinary skill in the art will readily appreciate there are numerous gene therapy vehicles that are capable of targeting a particular cell type and can therefore deliver a foreign nucleic acid specifically to those cells. For example, intravenous injection of DNA/liposome complexes to mice results in gene transfer and expression in numerous organs, including the bone marrow and the spleen (Zhu et al. "Systemic gene expression after intravenous DNA delivery into adult mice." Science 261:209–211 (1993)). This approach can be coupled with emerging technologies whereby hematopoietic cell-specific transduction has been achieved in vitro (Kasahara et al. "Tissue-specific targeting of retroviral vectors through ligand-receptor interactions." Science 266:1373–1376 (1994) and Schwarzenberger et al. "Targeted gene transfer to human hematopoietic progenitor cell lines through the c-kit receptor." Blood 87:472–478 (1996)). This procedure has the advantage, among others, of exposing the subject to fewer procedures such extraction of that subjects own hematopoietic progenitor cells and replacement of those cells after they have been genetically modified comprising introducing into those cells a nucleic acid encoding a dihydrofolate reductase which is relatively resistant to an antifolate. An additional major advantage of the method described here is that the in vivo modification would bypass the need for the toxic myeloablative conditioning that is necessary for engraftment in the autologous transplant setting.

The present invention therefore provides a method of in vivo selection for genetically modified hematopoietic progenitor cells from nonmodified hematopoietic cells in a subject comprising genetically modifying hematopoietic progenitor cells in the subject by introducing into the cells a nucleic acid comprising a sequence encoding a mutant dihydrofolate reductase which when expressed can confer antifolate resistance, administering to the subject an antifolate in an amount which inhibits the growth of the nonmodified hematopoietic cells, wherein the inhibition of the nonmodified hematopoietic cells by the antifolate can be offset in vivo by nucleoside salvage, and administering to the subject a suitable nucleoside transport inhibitor in an amount effective to prevent the offset of the inhibitory effect of the antifolate in the nonmodified hematopoietic cells, whereby the combination of the antifolate and the nucleoside transport inhibitor selects in vivo for the genetically modified hematopoietic progenitor cells.

This same method of genetically modifying hematopoietic cells within a subject and then selecting for these genetically modified cells using an antifolate in conjunction with a suitable nucleoside transport inhibitor can be performed by genetically modifying hematopoietic stem cells. The present invention therefore also provides a method of in vivo selection for genetically modified hematopoietic stem cells from nonmodified hematopoietic cells in a subject comprising genetically modifying hematopoietic stem cells in the subject by introducing into the cells a nucleic acid comprising a sequence encoding a mutant dihydrofolate reductase which when expressed can confer antifolate resistance, administering to the subject an antifolate in an amount which inhibits the growth of the nonmodified hematopoietic cells, wherein the inhibition of the nonmodified hematopoietic cells by the antifolate can be offset in vivo by nucleoside salvage, and administering to the subject a suitable nucleoside transport inhibitor in an amount effective to prevent the offset of the inhibitory effect of the antifolate in the nonmodified hematopoietic cells, whereby the combination of the antifolate and the nucleoside transport inhibitor selects in vivo for the genetically modified hematopoietic stem cells.

Utilities

Our system for in vivo selection of genetically modified hematopoietic cells has numerous potential applications. Any situation where the number of genetically-modified cells is insufficient will allow application of our system. Currently, most if not all gene therapy approaches directed at the primate hematopoietic system are limited by low rates of gene transfer. Therefore, in vivo selection with L22Y-DHFR and TMTX plus TTIs (thymidine transport inhibitors) can be used for any of these applications.

The most common method for the genetic alteration of cells of the hematopoietic system involves harvesting autologous stem cells either from the blood or from the bone marrow. These cells are then transduced with genetic vectors which may contain a therapeutic gene using a variety of in vitro culture conditions. After some period of time, the genetically altered cells are returned to the patient, typically after the patient undergoes myeloablative conditioning therapy. After patients recover from the conditioning therapy, the number of genetically-modified cells in hematopoietic compartments is very low and drops with time. The DHFR selection system can be applied at this time. Serial treatment courses with TMTX plus either NBMPR-P or draflazine can be given to enrich for primitive hematopoietic cells that express the DHFR-mutant. Ultimately, repeated rounds of selection can be used to eliminate most if not all cells which remained unmodified so that the genetically-modified cells comprise most if not all of the hematopoietic compartment.

The selection system can be applied to a number of genetic and acquired diseases by generating vectors that have a therapeutic gene linked to the DHFR-mutant gene. Post-transplant selection can then be used to enrich for cells that express the linked therapeutic gene. This approach involves the generation of selectable bicistronic vectors where one of the two genes is the DHFR-mutant gene. For example, a single retroviral promoter can direct the expression of the DHFR-mutant and a second gene, such as a therapeutic gene (e.g. MDR1), or a reporter gene (e.g. CD24). Alternatively, the vector may comprise an additional promoter which can direct the expression of a second gene, and the promoter or promoters can be designed to express only under certain conditions.

Sickle cell anemia is a disease amenable to treatment with this approach. This first step is to generate a vector that expresses both a therapeutic gene for sickle cell anemia and a drug resistant mutant of DHFR such as L22Y. Therapeutic genes for the hemoglobino-pathies such as a normal beta-like globin gene, or activator of gammaglobin transcription, can be incorporated in vectors with a drug resistant DHFR. A clinically certified, high titer retroviral producer clone can then be isolated for this vector. Patients with sickle cell anemia can then have hematopoietic cells collected, either from bone marrow aspirates or from mobilized peripheral blood samples. These cells can then be immunopurified for stem cells expressing the CD34 antigen using any one of several commercially available methods. The CD34+cells can then be transduced with retroviral supernatant using the best available transduction protocol. These protocols typically involve culturing bone marrow cells with retroviral supernatant in the presence of hematopoietic cytokines such as IL3, IL6, SCF, and FLT3 ligand. Some groups have used plates coated with fibronectin, while others have transduced cells in the presence of autologous stromal cells. Typically these transductions are done for 24–96 hours in the presence of a polycation such as protamine sulfate. Before reinfusion of the transduced cells, the patient will be treated with a conditioning regimen that is intended to reduce endogenous hematopoiesis and allow efficient engraftment of modified cells. Cancer patients typically receive high doses of cyclophosphamide and radiation although a variety of different conditioning regimens have been reported. After the conditioning regimen, the modified hematopoietic cells can be reinfused intravenously. Patients are supported while awaiting engraftment with hematopoietic cytokines such as G-CSF, intravenous antibiotics, transfusion products such as packed red blood cells, and other supportive means. After recovering from the myelosuppressive effects of the conditioning regimen, the number of genetically-corrected erythrocytes can be measured. The proportion of cells which express the transferred therapeutic gene will likely be much lower than that required to exert a significant clinical benefit, being estimated to be between 1 and 0.001% of all red blood cells. To enact in vivo selection of the corrected population, patients can then be treated with intravenous doses of TMTX and either NBMPR-P or draflazine. This selective therapy will amplify the genetically-corrected population of erythroid cells. Depending on the degree of amplification with each round of selection, patients may require serial rounds of selective treatment. This can be accomplished by allowing patients to recover from drug selection and then administering repeated doses of TMTX and transport inhibitors. This strategy will allow serial selection of corrected erythrocytes so that eventually the majority of erythrocytes will express the anti-sickling gene.

Our system for in vivo selection can be used not only for treatment of hemoglobinopathies, but for any genetic disease of myeloid cells. Candidates for this therapy include chronic granulomatous disease, Fanconi's anemia, red cell enzymopathies such as pyruvate kinase deficiency, and leukocyte adhesion deficiency. Because lysosomal storage diseases arise from defects in macrophages, diseases such as Gaucher's disease, mucopolysaccharidosis, Niemann-Pick type B, and metachromatic leukodystrophy can also be potential applications for the DHFR in vivo selection system. In general, any non-malignant genetic disease which is correctable by hematopoietic transplantation can be treated with selectable vectors which incorporate a linked therapuetic gene specific for the disease.

The combined use of DHFR mutants, antifolates, and transport inhibitors can also be used as a novel cancer therapy. In this embodiment, the DHFR vector can serve as a means to protect hematopoiesis from antifolate drugs used in the treatment of malignancy. The combined use of antifolates such as TMTX and transport inhibitors can increase the sensitivity of tumor cells to TMTX while providing selection of drug resistant cells within the bone marrow. The simultaneous chemosensitization of the tumor through the use of the transport inhibitor, and the protection of hematopoiesis conferred by the DHFR mutant such as L22Y-DHFR, leads to a widened therapeutic index and improved clinical response.

Because lymphoid cells are also progeny of hematopoietic stem cells, diseases of the immune system are also candidates for our in vivo selection system. Genetic correction of congenital immunodeficiency caused by adenosine deaminase deficiency (ADA), purine nucleoside phosphorylase deficiency, and JAK3 deficiency have all been potential applications for genetic therapy. In particular, patients with ADA deficiency who have been treated with genetically modified lymphocytes have been shown to have relatively low numbers of corrected cells in vivo. Application of the described selection methods of the present invention in any of these situations can enhance the immune correction by providing an increased number of functionally intact lymphoid cells.

Treatment of immunodeficiency resulting from acquired HIV infection with genetic vectors can be accomplished. In this strategy, an anti-HIV vector is targeted either to lymphocytes or to hematopoietic stem cells with intent to generate cells that are resistant to further infection with HIV. One strategy can be applied by developing a selectable anti-HIV vector by inserting the L22Y-DHFR cDNA into the construct. In vivo selection can then be used to enrich and expand normally functioning lymphoid cells that are resistant to HIV infection. The need to increase the number of HIV-resistant lymphocytes after gene therapy is highlighted by recent studies of HIV gene therapy.

Another application is the selection of cells used for adoptive immunotherapy. A number of investigators have been able to isolate and expand lymphocytes that react against proteins present on diseased cells. These cells are reinfused into the patient and contribute to elimination of the diseased cells. This approach has been used to treat disease in bone marrow transplant patients caused by Cytomegalovirus and Epstein Barr virus and is also being considered in a number of malignancies such as Hodgkins disease. The viral antigen specific lymphocytes can be transduced with DHFR selection vector. This strategy would allow selective amplification of the alloreactive lymphocytes in vivo and thereby allow modulation of the anti-disease response.

Throughout this application, various publications are referenced. The disclosures of these publications, and the references cited therein, in their entireties are hereby incorporated by reference into this application in order to more fully describe the state of the art to which this invention pertains.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and example be considered as exemplary only, with a true scope and spirit of the invention being indicated by the claims.

The following examples are set forth so as to provide those of ordinary skill in the art with a complete disclosure and description of how the methods claimed herein performed, and is intended to be purely exemplary of the invention and is not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in °C. and pressure is at or near atmospheric.

EXAMPLES

Resistance of Nonmodified Myeloid Progenitor Cells and Hematopoietic Stem Cells to an Antifolate To determine if the antifolate trimetrexate (TMTX), could be used to inhibit hematopoietic progenitor cells which had not been genetically modified to contain and express a mutant dihydrofolate reductase, we treated mice with high doses of TMTX and measured the myeloid progenitor and stem cell content in the bone marrow. Mice were intraperitoneally administered 100 or 130 mg/kg TMTX for five consecutive days. Bone marrow cellularity and progenitor content was examined relative to untreated mice 24 hrs after the final treatment. Despite severe marrow hypoplasia in TMTX treated mice, the number of myeloid progenitors and stem cells per femur remained the same in all groups of mice. Thus, although differentiated murine hematopoietic cells are highly sensitive to TMTX in vivo, immature myeloid progenitors resist it's cytotoxic effects.

The Mechanism by which Nonmodified Myeloid Hematopoietic Progenitors Escape Inhibition by an Antifolate We developed a defined in vitro liquid culture system to determine the mechanism by which murine myeloid progenitors escape killing with TMTX. This system involves the culture of unseparated murine bone marrow in medium supplemented with optimal concentrations of hematopoietic growth factors (IL-3 at 20 ng/ml, human IL-6 at 50 ng/ml, rat SCF at 50 ng/ml), and either undialyzed fetal bovine serum (FBS) or dialyzed FBS at 15% v/v final concentration, that has been depleted of detectable thymidine and hypoxanthine. The progenitor content is determined four days after culture initiation.

The number of progenitors in cultures without TMTX were similar using either dialyzed or undialyzed serum. However, TMTX addition (150 nM) allowed survival of at least 50% of the myeloid progenitors in cultures containing undialyzed serum compared to 5% progenitor survival in cultures containing dialyzed serum. Addition of high concentrations of thyrnidine (1.0 $\mu$M) alone did not restore TMTX resistance to progenitors in dialyzed serum. Likewise, addition of hypoxanthine (100 $\mu$M) alone to cultures containing dialyzed serum treated with thymidine phosphorylase did not rescue myeloid progenitors from TMTX toxicity. Addition of both thymidine and hypoxanthine fully restored myeloid progenitor survival to values observed without TMTX treatment. These data indicate that murine myeloid progenitors import both thymidine and hypoxanthine from the serum in order to circumvent drug-induced DHFR inhibition.

Figure 1B:
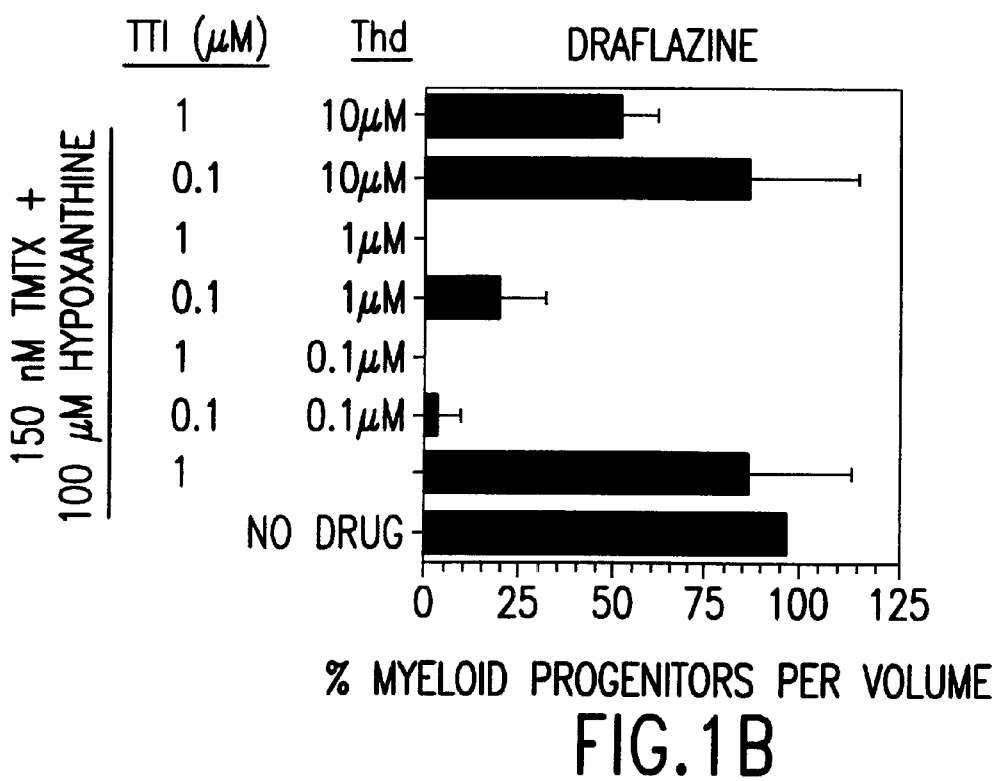

Use of a Thymidine Transport Inhibitor to Potentiate Antifolate Toxicity In vitro Thymidine transport inhibitors (TTI) were added to our defined liquid culture system. As shown in FIGS. 1A and 1B, the addition of either nitrobenzylmercaptopurine riboside (NBMPR) (at 1.0 $\mu$M or 0.1 $\mu$M) or draflazine (at 1.0 $\mu$M or 0.1 $\mu$M) to cultures containing 0.1 $\mu$M or 1 $\mu$M thymidine (approximate physiological serum concentrations in humans and mice, respectively) effectively sensitized progenitor cells to TMTX (150 nM). However, supraphysiological thymidine levels (10 $\mu$M) were able to overcome the TTI-specific blockage of thymidine import, restoring full progenitor survival. These data demonstrate that at physiological thymidine levels, both NBMPR and draflazine can be used to potentiate TMTX toxicity in unmodified myeloid progenitor cells and thereby provide a means for enrichment of resistant progenitor cells which contain and express the L22Y-DHFR vector.

Figure 2:
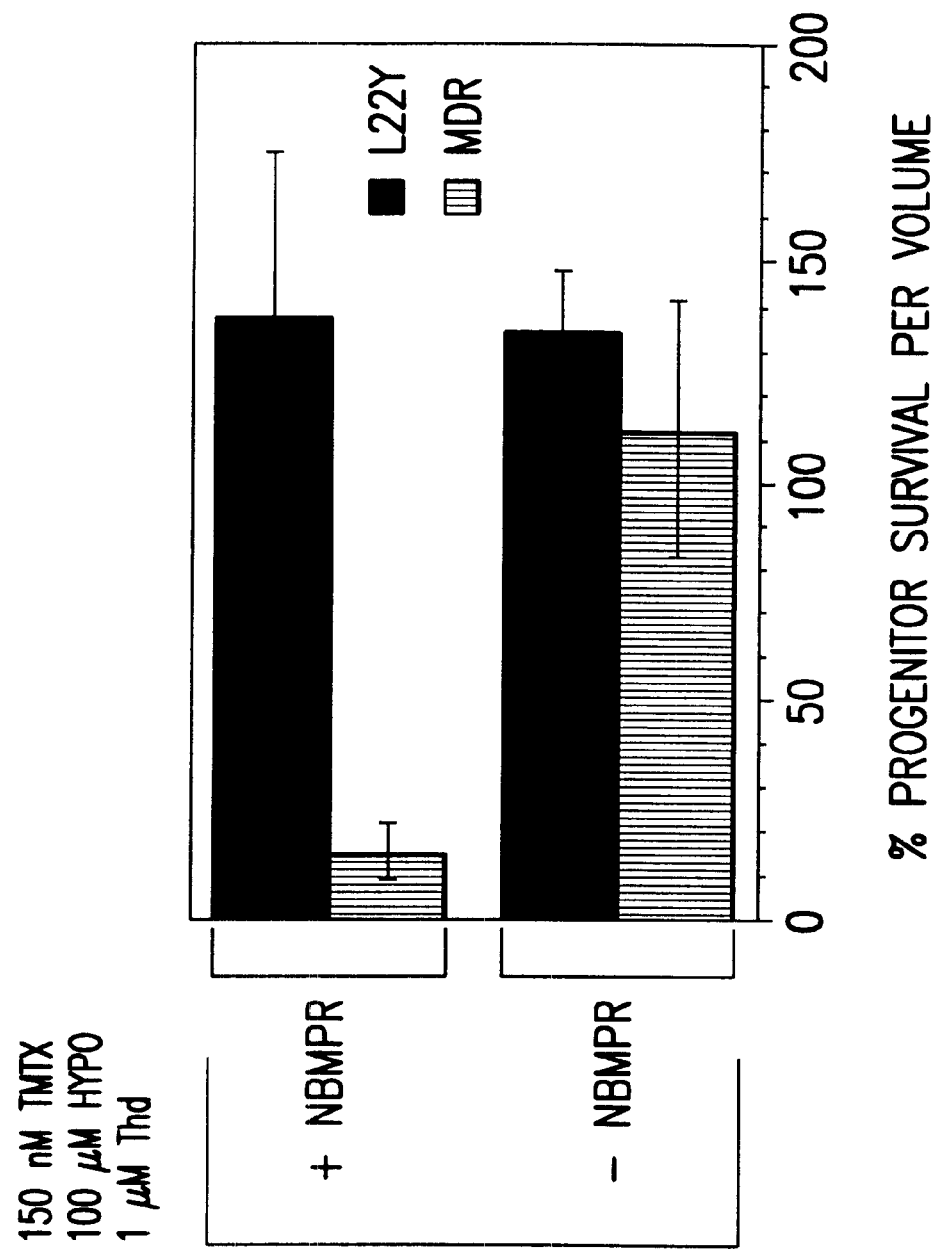
FIG. 2 shows L22Y-DHFR transduced progenitors are protected from TMTX+NBMPR toxicity in vitro. Unseparated bone marrow from C57B1/6 or WBBF$_1$+/+ mice was prestimulated for 48 hrs in medium supplemented with IL-3, IL-6 and SCF, and then layered on 100% confluent, irradiated L22Y-DHFR or control MDR1 ecotropic retroviral producers for an additional 48 hrs. Nonadherent marrow cells were then harvested, washed extensively in PBS and placed in a suspension culture system in DMEM supplemented with optimal concentrations of IL-3, IL-6 and SCF, and either undialyzed or dialyzed fetal bovine serum (FBS), with or without 1.0 $\mu$M NBMPR. Progenitor content was then assayed after four days of suspension culture as described in the legend to FIG. 1. Progenitor survival was scored relative to control cultures without TMTX addition.

To test if transfer of the L22Y-DHFR vector (Lewis et al. "Methotrexate-resistant variants of human dihydrofolate reductase with substitutions of leucine 22. Kinetics, crystallography, and potential as selectable markers." J.Biol.Chem. 270:5057–5064 (1995)) would protect murine myeloid progenitors from the combination of TMTX and NBMPR in vitro, transduced murine bone marrow cells were challenged with these drugs in our defined liquid culture system. As shown in FIG. 2, DHFR-modified progenitor cells grown in dialyzed serum supplemented with 1.0 $\mu$M thymidine, 100 $\mu$M hypoxanthine, and 150 nM trimetrexate, were completely resistant to TMTX and NBMPR (1.0 $\mu$M), whereas 85% of progenitor cells modified with a control virus were killed. Thus, murine myeloid progenitor cells can be sensitized to TMTX through the utilization of thymidine transport inhibitors and this toxicity can be completely reversed in vitro by expression of the L22Y-DHFR vector.

Figure 3A:
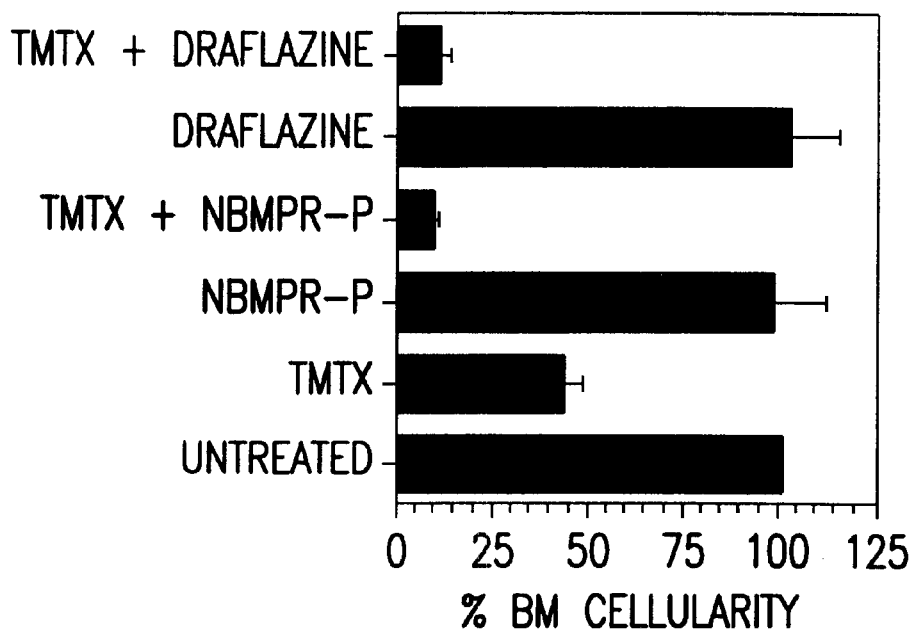
FIGS. 3a & 3b show thymidine transport inhibitors sensitize murine progenitors to TMTX in vivo Normal C57B1/6, WBBF$_1$+/+ or B6.C-H1$^6$/By (HW80) mice were administered TMTX (130 mg/kg), NBMPR-P (20 mg/kg) or draflazine (20 mg/kg) alone, or the combination of TMTX+ NBMPR-P or TMTX+draflazine ip for five consecutive days. 24 hrs following the last treatment, mice were sacrificed and bone marrow cellularity and myeloid progenitor content per femur were analyzed relative to untreated mice.
Figure 3B:
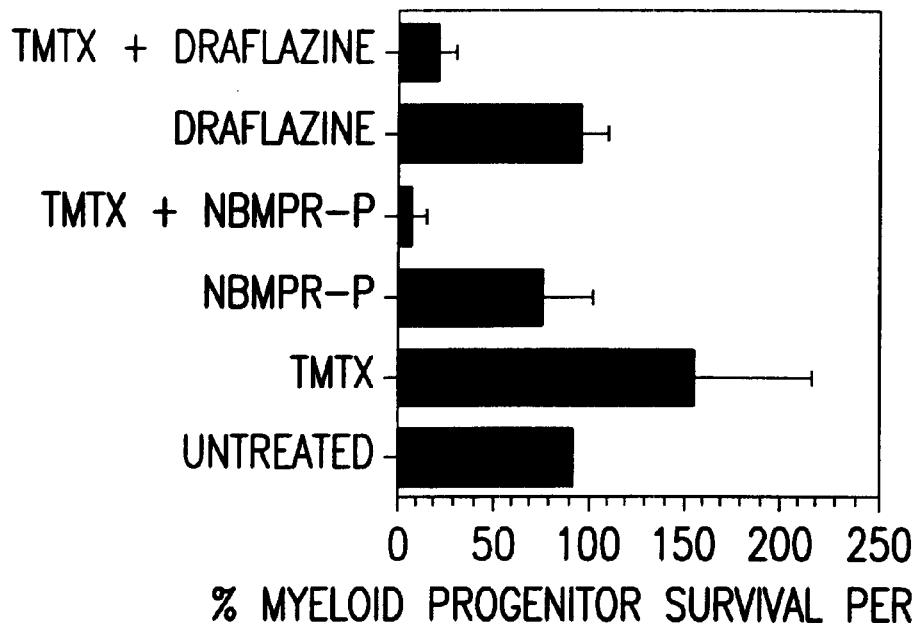

In vivo Sensitization of Nonmodified Myeloid Hematopoietic Progenitor Cells to TMTX and TTIs In order to determine whether the combination of TMTX and TTIs will kill murine myeloid progenitors in vivo, normal mice were intraperitoneally administered TMTX (130 mg/kg) together with either NBMPR-5' monophosphate (NBMPR-P) (20 mg/kg) or draflazine (20 mg/kg) for five consecutive days. 24 hrs after the last treatment, the combination of TMTX and either NBMPR-P or draflazine reduced marrow cellularity to a greater degree than TMTX alone, while neither TTI alone had any measurable effect on marrow cellularity (FIG. 3A). The myeloid progenitor content in the marrow was also measured following these various treatments. As shown in FIG. 3B, the administration of TMTX alone actually resulted in a modest increase in the number of myeloid progenitors. Treatment with either of NBMPR-P or draflazine alone had no effect on progenitor survival, however the combination of TMTX and either TTI severely reduced the number of myeloid progenitors relative to untreated control mice. Thus, while TMTX alone is insufficient for the killing of myeloid progenitors in vivo, either draflazine or NBMPR-P can be used to sensitize progenitors to TMTX thereby allowing elimination of unmodified cells in vivo.

In vivo Selection of Myeloid Hematopoietic Progenitors Using a DHFR Mutant

Figure 4A:
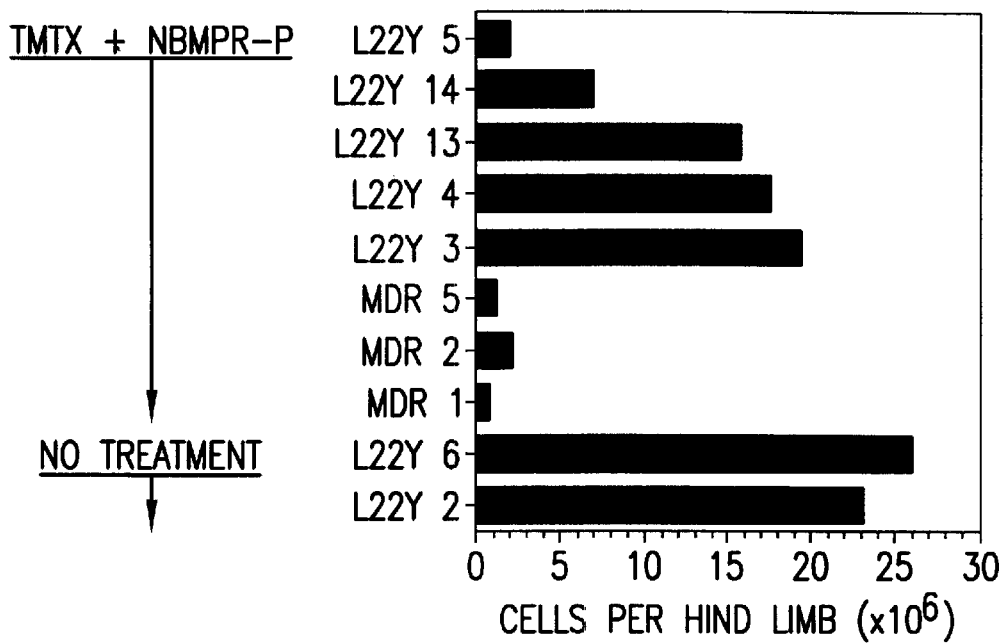
FIGS. 4a & 4b show in vivo protection of L22Y-DHFR modified bone marrow cells (4A) and progenitors (4B) in mice treated with TMTX+NBMPR-P. 48 hrs after treatment with 150 mg/kg 5-FU, bone marrow was harvested from C57B1/6 mice and prestimulated and transduced with L22Y-DHFR or MDR1 retroviral vectors. 2×10$^6$ transduced marrow cells were then transplanted into genetically anemic W/W$^V$ mice. Transplanted normal donor cells competitively reconstitute host hematopoiesis completely due to the defective c-kit receptor expressed on host hematopoietic cells. 6 months after transplantation, mice were administered TMTX+NBMPR-P for five consecutive days. 24 hrs following the final treatment, bone marrow cellularity (4A) and hind limb progenitor (4B) content were analyzed relative to untreated transplanted mice.
Figure 4B:
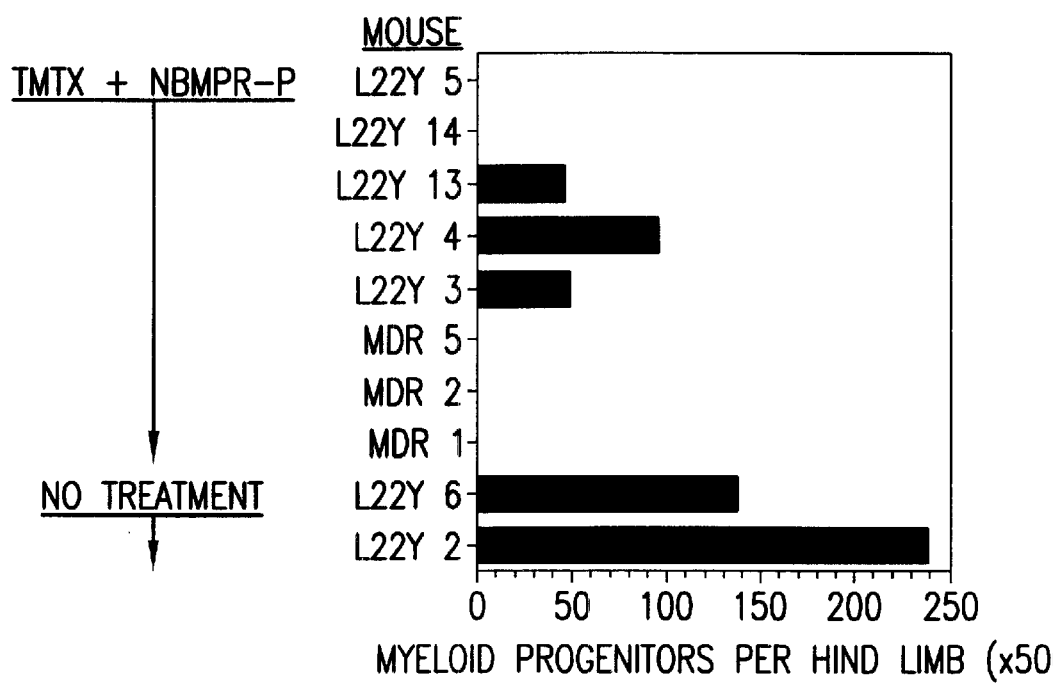

To determine whether this strategy could be used for in vivo selection of myeloid progenitors expressing the L22Y-DHFR vector, mice transplanted with L22Y-DHFR or control (MDR1) transduced bone marrow were intraperitoneally administered TMTX (130 mg/kg) and NBMPR-P (20 mg/kg) for five consecutive days. As shown in FIG. 4A, 24 hrs after the last treatment, all of the MDR1 mice had large reductions in marrow cellularity while the marrow cellularity was preserved in 3 of 5 L22Y-DHFR mice. In these L22Y-DHFR mice, a significant number of myeloid progenitors survived the dual drug treatment while there were no surviving progenitors in treated control mice. Between 23,000 and 48,000 progenitor cells were present in the hind limbs of 3 L22Y-DHFR animals (FIG. 4B). These data show that transfer of the L22Y-DHFR vector into myeloid progenitor cells provides in vivo protection against the combined use of TMTX and NBMPR-P.

Figure 5:
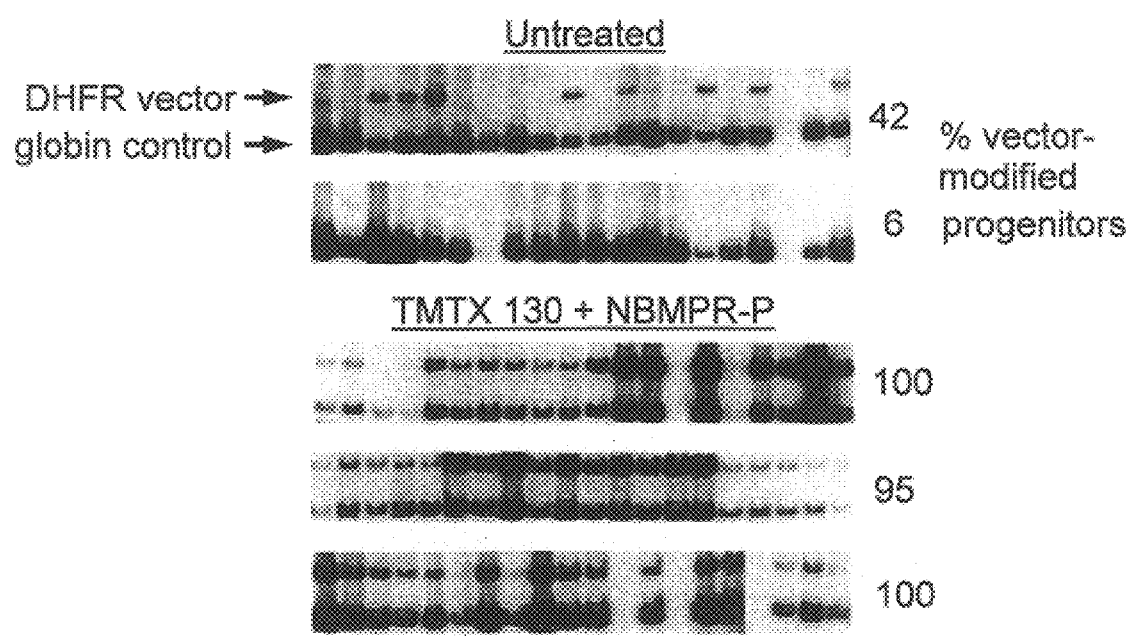
FIG. 5 shows evidence for in vivo selection of L22Y-DHFR transduced myeloid progenitors in mice treated with TMTX+NBMPR-P 6 months after transplant. Individual progenitor-derived colonies isolated from methylcellulose plates from untreated or TMTX+NBMPR-P treated mice were examined by PCR for presence of integrated provirus (L22Y-DHFR vector). Primers specific for the endogenous mouse $\beta$-globin gene were used as an internal control (globin control).

To address the question of whether the combination TMTX and NBMPR-P treatment enriches for progenitor cells transduced with the L22Y-DHFR vector, individual myeloid colonies from treated and untreated DHFR-L22Y mice were examined for evidence of the DHFR vector. A PCR assay (Allay et al. "Retroviral transduction and expression of the human alkyltransferase cDNA provides nitrosourea resistance to hematopoietic cells." Blood 85:3342–3351 (1995)) was used for detection of the integrated vector and indicated that 54/55 (98%) of the colonies derived from treated mice were positive for presence of the L22Y-DHFR, while only 9/37 (24%) of the colonies derived from the mice that did not receive TMTX and NBMPR-P contained the L22Y-DHFR vector (FIG. 5). This experiment provides direct evidence that dual drug treatment selectively enriches for L22Y-DHFR-modified myeloid progenitors in vivo.

The above experiments indicate that the combination of an antifolate (TMTX) and TTIs effectively eliminates unmodified myeloid progenitors. Although selection at the progenitor level should be useful in a number of circumstances, selection at the level of repopulating stem cells should give the most durable and stable selection of vectormodified cells. To test if the combination of TMTX and NBMPR-P could be used to kill unmodified stem cells, C57B1/6J mice were treated with various drug combinations (intraperitoneal injections at the following doses: trimetrexate at 130 mg/kg, NBMPR-P at 20 mg/kg, and draflazine at 20 mg/kg) and then used as donors for bone marrow transplantation. Stem cell viability was measured by hemoglobin electrophoresis patterns in W/W$_v$ mice used as transplant recipients. In this model, viable stem cells can repopulate W/W$_v$ mice which have genetically defective stem cells.

Figure 6:
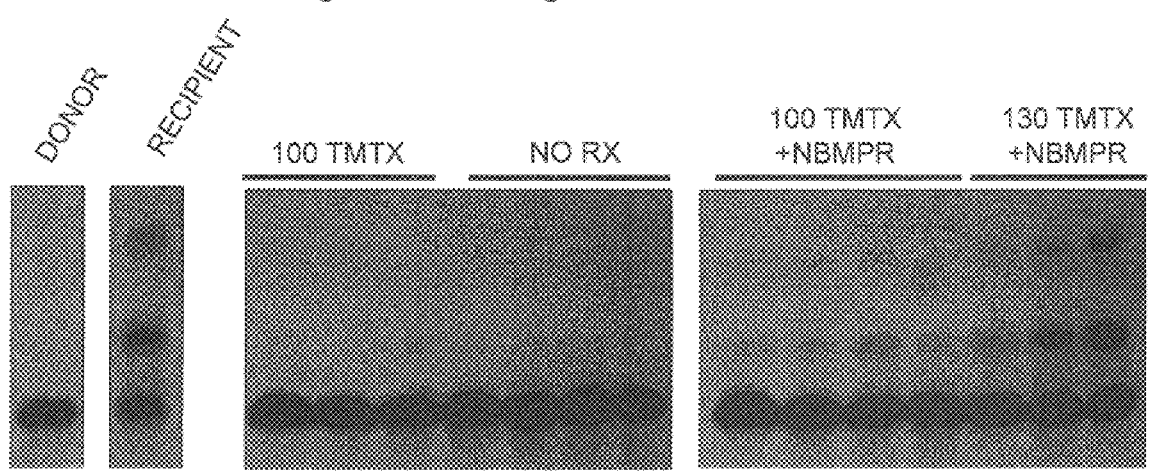
FIG. 6 shows TMTX and NBMPR-P kill hematopoietic stem cells in normal mice. C57B1/6 donor mice were administered either 100 mg/kg TMTX, 100 mg/kg TMTX+ 20 mg/kg NBMPR-P, or 130 mg/kg TMTX+20 mg/kg NBMPR-P ip for five consecutive days. 24 hrs following the last treatment, bone marrow was harvested and transplanted into genetically anemic W/W$^V$ mice. The hemoglobin phenotype of transplanted mnice was determined after 8 weeks. Bone marrow from either untreated mice or mice that received treatments that did not kill stem cells completely repopulated recipients, as evidenced by the absence of the host hemoglobin phenotype. Bone marrow from donor mice that received treatments that were cytotoxic to stem cells failed to reconstitute host hematopoiesis, as evidenced by the maintenance of the host hemoglobin phenotype.

Repopulation can be monitored by hemoglobin electrophoresis, which can distinguish the pattern obtained from C57B1/6J erthryocytes versus the W/W$_v$ background. FIG. 6 shows five daily doses of TMTX at 100 mg/kg/day failed to adversely effect the hematopoietic repopulating ability of donor marrow. In contrast, when mice were treated for five consecutive days with the combination of 130 mg/kg TMTX and 20 mg/kg NBMPR-P, repopulating capacity of donor marrow was significantly reduced, as indicated by the recipient hemoglobin pattern after transplant. Marrow derived from donor mice treated with 100 mg/kg TMTX and 20 mg/kg NBMPR-P had intermediate repopulating ability. Analysis of thymic reconstitution by Southern blot confirmed that TMTX and NBMPR-P eliminated cells capable of repopulating both lymphoid and myeloid lineages. Thus, while TMTX alone does not appear to be sufficient for in vivo selection of hematopoietic stem or progenitor cells, the combination of TMTX and NBMPR-P effectively depletes both nonmodified progenitor cells and nonmodified repopulating stem cells.

In vitro Protection of Human Hematopoietic Progenitor Cells

Figure 7:
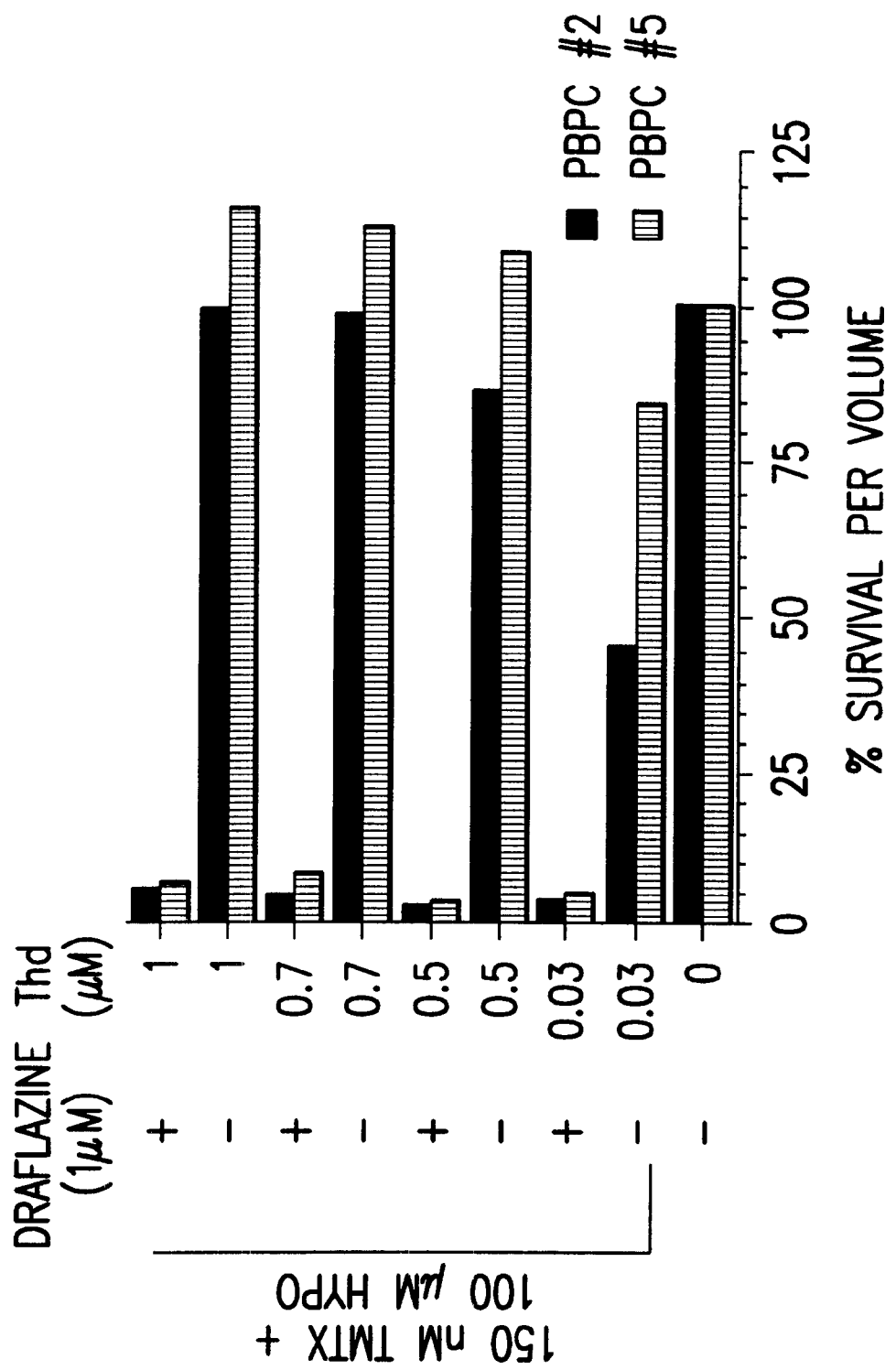
FIG. 7 shows draflazine potentiates TMTX toxicity in human myeloid progenitors. CD34-enriched, mobilized peripheral blood progenitors were assayed in the defined suspension culture system, as described for murine cells in the legend to FIG. 1. Two separate human samples were examined, and progenitor survival is represented relative to progenitors cultured without TMTX.

We examined the ability of draflazine to potentiate TMTX toxicity of human CD34 immunoselected progenitors in our defined liquid culture system comprising 15% dialyzed fetal calf serum, 20 ng/ml human IL-3, 50 ng/ml human IL-6, and 50 ng/ml human SCF in the presence-or absence of 1.0 $\mu$M draflazine, 100 $\mu$M hypoxanthine, 150 nM trimetrexate, and varying concentrations of thymidine ranging from 0 to 1.0 micromolar. FIG. 7 shows the results of two separate human CD34-enriched peripheral blood progenitor samples cultured in the presence or absence of draflazine at varying concentrations of thymidine. CD34 selection was done using a Ceprate cell column (CellPro) according to the manufacturers instructions. Similar to the results observed for murine myeloid progenitors described above, draflazine effectively potentiated TMTX toxicity in the presence of varying concentrations of thymidine. Thus, similar to their murine counterparts, these experiments demonstrate that draflazine can potentiate TMTX toxicity in nonmodified human myeloid progenitors at physiologic thymidine concentrations.

We have generated a high titer ($\geq 1 \times 10^7$ TMTX) CFU/ml) amphotropic L22Y DHFR retroviral producer clone, enabling us to determine whether human hematopoietic progenitors can acquire TMTX resistance after L22Y-DHFR modification. Human progenitor cells were transduced as follows. Mononuclear cells were isolated by passing peripheral blood cells over a Ficoll gradient. These cells were cultured at $5 \times 10^5$ cells/ml in the presence of human IL-3 at 20 ng/ml, human IL-6 at 50 ng/ml, and human SCF at 50 ng/ml and 15% v/v fetal calf serum. After 48 hours, these cells were placed on plates containing an irradiated confluent layer of fibroblasts that were producing the amphotropic L22Y vector. The cytokine concentrations during this coculture period were identical to that used during the previous prestimulation phase. Protamine sulfate was also included during the coculture phase at a concentration of 4 µg/ml. After 48 hours of coculture, cells were washed and plated in semisolid media obtained from Stem Cell Technologies according to manufacturers specifications. This media was pretreated with thymidine phosphorylase at 1 unit/3 ml of media. Trimetrexate was added to this media at concentrations ranging from 0 to 500 ng/ml.

Figure 8:
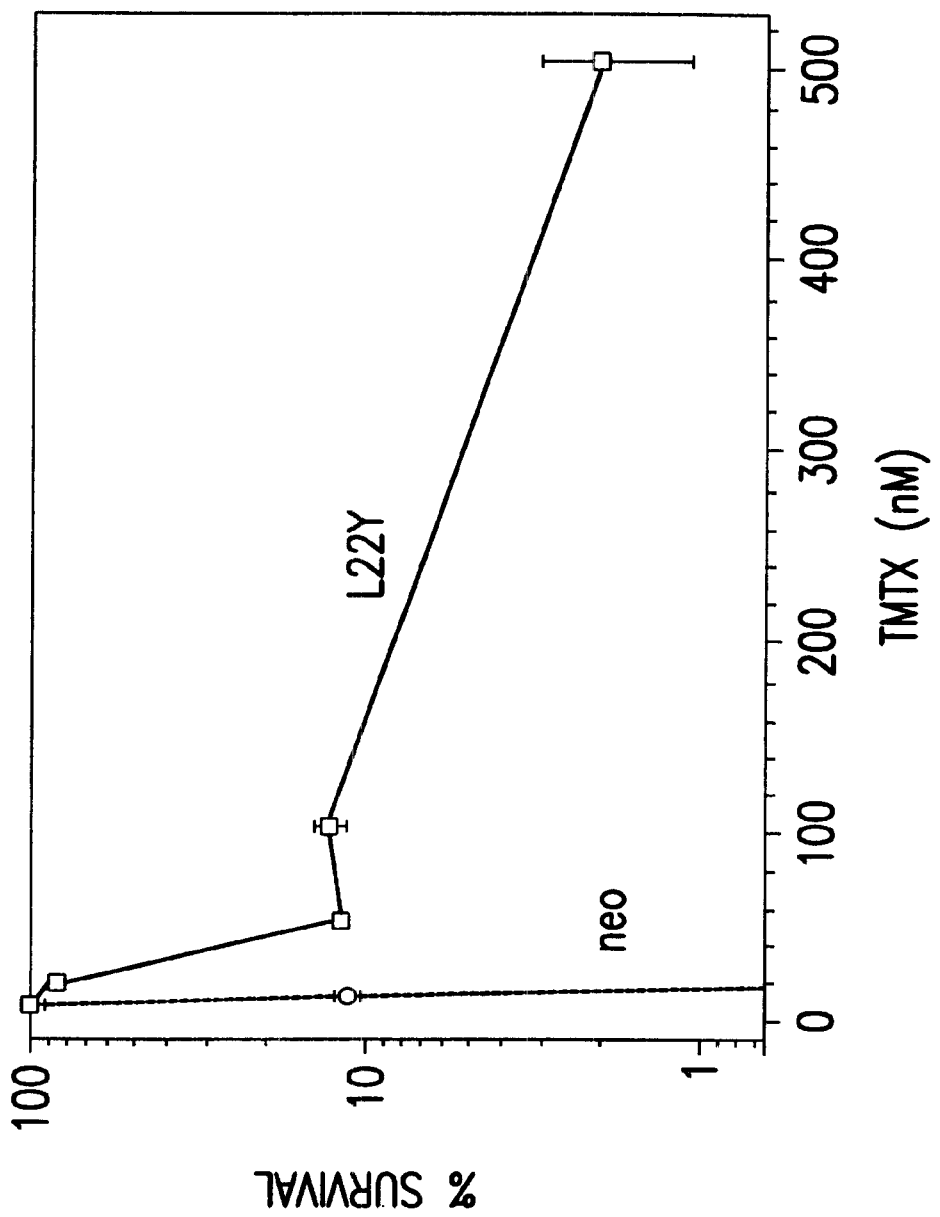
FIG. 8 shows L22Y-DHFR-transduced human myeloid progenitors have increased TMTX resistance in vitro. Peripheral blood cells collected following chemotherapy and growth factor mobilization were prestimulated for 48 hrs with IL-3, IL-6 and SCF, followed by coculture on irradiated amphotropic retroviral producers (L22Y-DHFR or neo) for an additional 48 hrs. Nonadherent hematopoietic cells were then assayed for drug resistant progenitors by addition of increasing concentrations of TMTX to the semisolid methylcellulose cultures.

FIG. 8 shows that following coculture with amphotropic L22Y-DHFR producer cells in medium that has been supplemented with human interleukin-3, human interleukin-6, human stem cell factor and protamine sulphate, mobilized human peripheral blood progenitor cells had increased TMTX-resistance relative to control (neo) transduced progenitor cells. Thus, since L22Y-DHFR effectively transduces and expresses within human myeloid progenitor cells, in vivo selection of human hematopoietic cells can occur in a manner analogous to that demonstrated in the murine system.

In summary, we have invented a novel system for in vivo selection of primitive hematopoietic cells that have been transduced with retroviral vectors. This system involves the novel combination of a unique retroviral vector containing an optimized DHFR resistance gene, and the combined use of trimetrexate with either NBMPR-P or draflazine, both which inhibit thymidine transport. We have shown that this combination gives dramatically improved selection of vector-transduced myeloid progenitors in vivo. Since dual drug treatment can eliminate unmodified stem cells, this approach can also be used to enact selection at the stem cell level. Moreover, this selection method can be used for gene therapy where a therapeutic gene is included in the DHFR vector.

What is claimed is:

1. A method of in vivo selection for genetically modified hematopoietic progenitor cells from nonmodified hematopoietic cells in a subject comprising:
    a. genetically modifying hematopoietic progenitor cells by introducing into the cells a nucleic acid comprising a sequence encoding a mutant dihydrofolate reductase which when expressed can confer antifolate resistance;
    b. administering to the subject the genetically modified hematopoietic progenitor cells;
    c. administering to the subject an antifolate in an amount which inhibits the growth of the nonmodified hematopoietic cells, wherein the inhibition of the nonmodified hematopoietic cells by the antifolate can be offset in vivo by nucleoside salvage; and
    d. administering to the subject a suitable nucleoside transport inhibitor in an amount effective to prevent the offset of the inhibitory effect of the antifolate in the nonmodified hematopoietic cells, whereby the combination of the antifolate and the nucleoside transport inhibitor selects in vivo for the genetically modified hematopoietic progenitor cells.

2. The method of claim 1, wherein the nucleic acid further comprises a heterologous gene.

3. The method of claim I, wherein the mutant dihydrofolate reductase contains a tyrosine at codon 22.

4. The method of claim 1, wherein the mutant dihydrofolate reductase contains an arginine at codon 31.

5. The method of claim 1, wherein the mutant dihydrofolate reductase contains a tyrosine at codon 22 and an arginine at codon 31.

6. The method of claim 1, wherein the antifolate is selected from the group consisting of trimetrexate and methotrexate.

7. The method of claim 1, wherein the mutant dihydrofolate reductase contains a tyrosine at codon 22 and the antifolate is trimetrexate.

8. The method of claim 1, wherein the mutant dihydrofolate reductase contains a tyrosine at codon 22 and an arginine at codon 31 and the antifolate is trimetrexate.

9. The method of claim 1, wherein the nucleoside transport inhibitor is the 5' monophosphate derivative of nitrobenzylmercaptopurine riboside.

10. The method of claim 1, wherein the nucleoside transport inhibitor is selected from the group consisting of dilazep and draflazine.

11. The method of claim 1, wherein the genetically modified hematopoietic progenitor cells administered to the subject are autologous.

12. The method of claim 1, wherein the subject is a human.

13. A method of in vivo selection for genetically modified hematopoietic stem cells from nonmodified hematopoietic stem cells in a subject comprising:
    a. genetically modifying hematopoietic stem cells by introducing into the cells a nucleic acid comprising a sequence encoding a mutant dihydrofolate reductase which when expressed can confer antifolate resistance,
    b. administering to the subject the genetically modified hematopoietic stem cells,
    c. administering to the subject an antifolate in an amount which inhibits the growth of the nonmodified hematopoietic stem cells, wherein the inhibition of the nonmodified hematopoietic stem cells by the antifolate can be offset in vivo by nucleoside salvage; and
    d. administering to the subject a suitable nucleoside transport inhibitor in an amount effective to prevent the offset of the inhibitory effect of the antifolate in the nonmodified hematopoietic stem cells, whereby the combination of the antifolate and the nucleoside transport inhibitor selects in vivo for the genetically modified hematopoietic stem cells.

14. The method of claim 13, wherein the nucleic acid further comprises a heterologous gene.

15. The method of claim 13, wherein the mutant dihydrofolate reductase contains a tyrosine at codon 22.

16. The method of claim 13, wherein the mutant dihydrofolate reductase contains an arginine at codon 31.

17. The method of claim 13, wherein the mutant dihydrofolate reductase contains a tyrosine at codon 22 and an arginine at codon 31.

18. The method of claim 13, wherein the antifolate is selected from the group consisting of trimetrexate and methotrexate.

19. The method of claim 13, wherein the mutant dihydrofolate reductase contains a tyrosine at codon 22 and the antifolate is trimetrexate.

20. The method of claim 13, wherein the mutant dihydrofolate reductase contains a tyrosine at codon 22 and an arginine at codon 31 and the antifolate is trimetrexate.

21. The method of claim 13, wherein the nucleoside transport inhibitor is the 5' monophosphate derivative of nitrobenzylmercaptopurineriboside.

22. The method of claim 13, wherein the nucleoside transport inhibitor is selected from the group consisting of dizep and draflazine.

23. The method of claim 13, wherein the genetically modified hematopoietic stem cells administered to the subject are autologous.

24. The method of claim 13, wherein the subject is a human.

25. A method of in vivo selection for hematopoietic progenitor cells genetically modified to contain and express a nucleic acid comprising a sequence encoding an antifolate resistant dihydrofolate reductase from nonmodified hematopoietic cells in a subject comprising:
   a. administering to the subject the genetically modified hematopoietic progenitor cells;
   b. administering to the subject an antifolate in an amount which inhibits the growth of the nonmodified hematopoietic cells, wherein the inhibition of the nonmodified hematopoietic cells by the antifolate can be offset in vivo by nucleoside salvage; and
   c. administering to the subject a suitable nucleoside transport inhibitor in an amount effective to prevent the offset of the inhibitory effect of the antifolate in the nonmodified hematopoietic cells, whereby the combination of the antifolate and the nucleoside transport inhibitor selects in vivo for the genetically modified hematopoietic progenitor cells.

26. A method of in vivo selection for hematopoietic stem cells genetically modified to contain and express a nucleic acid comprising a sequence encoding an antifolate resistant dihydrofolate reductase from nonmodified hematopoietic stem cells in a subject comprising:
   a. administering to the subject the genetically modified hematopoietic stem cells;
   b. administering to the subject an antifolate in an amount which inhibits the growth of the nonmodified hematopoietic stem cells, wherein the inhibition of the nonmodified hematopoietic stem cells by the antifolate can be offset in vivo by nucleoside salvage; and
   c. administering to the subject a suitable nucleoside transport inhibitor in an amount effective to prevent the offset of the inhibitory effect of the antifolate in the nonmodified hematopoietic stem cells, whereby the combination of the antifolate and the nucleoside transport inhibitor selects in vivo for the genetically modified hematopoietic stem cells.

27. A method of in vivo selection for genetically modified hematopoietic progenitor cells from nonmodified hematopoietic cells in a subject comprising:
   a. genetically modifying hematopoictie progenitor cells in the subject by introducing into the cells a nucleic acid comprising a sequence encoding a mutant dihydrofolate reductase which when expressed can confer antifolate resistance;
   b. administering to the subject an antifolate in an amount which inhibits the growth of the nonmodified hematopoictic cells, wherein the inhibition of the nonmodified hematopoietic cells by the antifolate can be offset in vivo by nucleoside salvage; and
   c. administering to the subject a suitable nucleoside transport inhibitor in an amount effective to prevent the offset of the inhibitory effect of the antifolate in the nonmodified hematopoietic cells, whereby the combination of the antifolate and the nucleoside transport inhibitor selects in vivo for the genetically modified hematopoietic progenitor cells.

28. A method of in vivo selection for genetically modified hematopoietic stem cells from nonmodified hematopoietic cells in a subject comprising:
   a. genetically modifying hematopoietic stem cells in the subject by introducing into the cells a nucleic acid comprising a sequence encoding a mutant dihydrofolate reductase which when expressed can confer antifolate resistance;
   b. administering to the subject an antifolate in an amount which inhibits the growth of the nonmodified hematopoietic cells, wherein the inhibition of the nonmodified hematopoietic cells by the antifolate can be offset in vivo by nucleoside salvage; and
   c. administering to the subject a suitable nucleoside transport inhibitor in an amount effective to prevent the offset of the inhibitory effect of the antifolate in the nonmodified hematopoietic cells, whereby the combination of the antifolate and the nucleoside transport inhibitor selects in vivo for the genetically modified hematopoietic stem cells.

* * * * *